(12) United States Patent
Heidenhain et al.

(10) Patent No.: US 9,676,900 B2
(45) Date of Patent: Jun. 13, 2017

(54) FLUORENE CONTAINING COPOLYMER USED IN LIGHT EMITTING DEVICES

(75) Inventors: Sophie Barbara Heidenhain, Cambridgeshire (GB); Matthew Roberts, Cambridge (GB); Michael Cass, Cambridge (GB); Natasha M. J. Conway, Cambridge (GB); Fredrik Jakobsson, Cambridge (GB)

(73) Assignees: Cambridge Display Technology, Ltd., Godmanchester (GB); Sumitomo Chemical Company Limited, Tokyo (JP)

( * ) Notice: Subject to any disclaimer, the term of this patent is extended or adjusted under 35 U.S.C. 154(b) by 850 days.

(21) Appl. No.: 13/982,729

(22) PCT Filed: Jan. 31, 2012

(86) PCT No.: PCT/GB2012/050207
§ 371 (c)(1),
(2), (4) Date: Nov. 13, 2013

(87) PCT Pub. No.: WO2012/104628
PCT Pub. Date: Aug. 9, 2012

(65) Prior Publication Data
US 2015/0307652 A1    Oct. 29, 2015

(30) Foreign Application Priority Data

Jan. 31, 2011 (GB) .................................. 1101641.7
Jul. 4, 2011 (GB) .................................. 1111375.0
(Continued)

(51) Int. Cl.
*H01L 51/50* (2006.01)
*C08G 61/02* (2006.01)
(Continued)

(52) U.S. Cl.
CPC .............. *C08G 61/02* (2013.01); *C07C 25/22* (2013.01); *C07C 25/24* (2013.01); *C07C 211/61* (2013.01);
(Continued)

(58) Field of Classification Search
CPC ...................... C08G 2261/3142; C07D 401/04
See application file for complete search history.

(56) References Cited

U.S. PATENT DOCUMENTS

2005/0214568 A1* 9/2005 Wang et al. ......... C07D 401/04
428/690
2006/0121314 A1  6/2006 Choi et al.
2006/0284140 A1  12/2006 Breuning et al.

FOREIGN PATENT DOCUMENTS

CN    101168662 A    4/2008
EP    0 259 229 A1    3/1988
(Continued)

OTHER PUBLICATIONS

Berthelot et al. Anodic polymerization of difluorenyls linked with polyether or alkyl spacers: synthesis of polyfluorenes with complexing properties, Synthetic Metals, 75, 1995, p. 11-23.*
(Continued)

*Primary Examiner* — Francisco Tschen
(74) *Attorney, Agent, or Firm* — Wolf, Greenfield & Sacks, P.C.

(57) ABSTRACT

A polymer comprising a repeat unit of formula (I): (I) wherein $Ar^6$ and $Ar^7$ each independently represent a substituted or unsubstituted aryl or heteroaryl group; Sp represents a spacer group comprising a chain of at least 2 aliphatic carbon atoms spacing $Ar^6$ from $Ar^7$; m is at least 1; and if m is greater than 1 then —$(Ar^7)$m forms a linear or branched chain of $Ar^7$ groups in which $Ar^7$ in each occurrence may be the same or different.

(Continued)

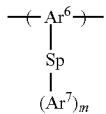

(I)

11 Claims, 4 Drawing Sheets

(30) Foreign Application Priority Data

Nov. 2, 2011 (GB) .................................... 1118941.2
Nov. 22, 2011 (GB) .................................... 1120131.6
Dec. 23, 2011 (GB) .................................... 1122316.1

(51) Int. Cl.
| | |
|---|---|
| *C08G 61/12* | (2006.01) |
| *C09K 11/06* | (2006.01) |
| *H01L 51/00* | (2006.01) |
| *H05B 33/14* | (2006.01) |
| *C07C 211/61* | (2006.01) |
| *C07F 5/04* | (2006.01) |
| *C07C 25/22* | (2006.01) |
| *C07C 25/24* | (2006.01) |

(52) U.S. Cl.
CPC .............. *C07F 5/04* (2013.01); *C08G 61/12* (2013.01); *C09K 11/06* (2013.01); *H01L 51/0039* (2013.01); *H01L 51/0043* (2013.01); *H05B 33/14* (2013.01); *C07C 2102/06* (2013.01); *C07C 2103/18* (2013.01); *C08G 2261/12* (2013.01); *C08G 2261/148* (2013.01); *C08G 2261/1412* (2013.01); *C08G 2261/312* (2013.01); *C08G 2261/314* (2013.01); *C08G 2261/3142* (2013.01); *C08G 2261/3162* (2013.01); *C08G 2261/411* (2013.01); *C08G 2261/512* (2013.01); *C08G 2261/5222* (2013.01); *C08G 2261/95* (2013.01); *C09K 2211/1416* (2013.01); *H01L 51/5012* (2013.01); *H01L 51/5056* (2013.01)

(56) References Cited

FOREIGN PATENT DOCUMENTS

| EP | 2 308 910 A1 | 4/2011 |
| WO | WO 02/092724 A1 | 11/2002 |
| WO | WO 2010/013723 A1 | 2/2010 |

OTHER PUBLICATIONS

International Search Report and Written Opinion for Application No. PCT/GB2012/050207 mailed Jul. 25, 2012.
International Preliminary Report on Patentability for Application No. PCT/GB2012/050207 dated Aug. 6, 2013.
He et al., Highly fluorescent intramolecular dimmers of two pyrenyl-substituted fluorenes bridged by 1,6-hexanyl: synthesis, spectroscopic, and self-organized properties. Tetrahedron Lett. 2010; 51(9):1317-21.
Siedle et al., Synthesis of unsymmetrical ansa-fluorenyl metallocenes. J Molec Catalysis A: Chem. 2004; 214(2):187-98.
Setayesh et al., Polyfluorenes with polyphenylene dendron side chains: toward non-aggregating, light-emitting polymers. J Am Chem Soc. Feb. 7, 2001;123(5):946-53.

* cited by examiner

FLUORENE CONTAINING COPOLYMER USED IN LIGHT EMITTING DEVICES

RELATED APPLICATIONS

The present application is a national stage filing under 35 U.S.C. §371 of international PCT application, PCT/GB2012/050207, filed Jan. 31, 2012, which claims priority to United Kingdom patent application, GB 1101641.7, filed Jan. 31, 2011, United Kingdom patent application, GB 1111375.0, filed Jul. 4, 2011, United Kingdom patent application, GB 1118941.2, filed Nov. 2, 2011, United Kingdom patent application, GB 1120131.6, filed Nov. 22, 2011, and United Kingdom patent application, GB 1122316.1, filed Dec. 23, 2011, each of which is incorporated herein by reference.

FIELD OF THE INVENTION

The present invention relates to polymers, methods of making said polymers and devices comprising said polymers.

BACKGROUND

Electronic devices comprising active organic materials are attracting increasing attention for use in devices such as organic light emitting diodes (OLEDs), organic photoresponsive devices (in particular organic photovoltaic devices and organic photosensors), organic transistors and memory array devices. Devices comprising organic materials offer benefits such as low weight, low power consumption and flexibility. Moreover, use of soluble organic materials allows use of solution processing in device manufacture, for example inkjet printing or spin-coating.

An OLED may comprise a substrate carrying an anode, a cathode and one or more organic light-emitting layers between the anode and cathode. One or more organic charge transporting and/or one or more charge blocking layers may also be provided between the anode and cathode.

Holes are injected into the device through the anode and electrons are injected through the cathode during operation of the device. Holes in the highest occupied molecular orbital (HOMO) and electrons in the lowest unoccupied molecular orbital (LUMO) of a light-emitting material in the light-emitting layer combine to form an exciton that releases its energy as light. Singlet excitons may undergo radiative decay to produce fluorescence; triplet excitons may be caused undergo radiative decay in the presence of suitable dopant, for example a heavy transition metal complex, to produce phosphorescence.

Suitable light-emitting materials include small molecule, polymeric and dendrimeric materials. Suitable light-emitting polymers for use in layer 3 include poly(arylene vinylenes) such as poly(p-phenylene vinylenes) and polyarylenes such as polyfluorenes.

Polymers comprising 9,9-dialkyl substituted fluorene repeat units are disclosed in, for example, WO 99/54385.

WO 02/092723 discloses polymers comprising 9,9-diaryl substituted fluorene repeat units, which are reported to have longer lifetime that analogous polymers comprising 9,9-dialkyl substituted fluorene repeat units. This increased lifetime is attributed to an increase in thermal stability of the polymer when 9,9-dialkyl substituents are replaced with 9,9-diaryl substituents, which is manifested in higher polymer glass transition temperatures ("lifetime" as used herein means the time taken for luminance of a polymer to fall by a specified percentage, for example 10% or 50%, at constant current).

DE 19846767 discloses a 9-alkyl-9-aryl fluorene monomer.

WO 2004/039912 discloses a method of forming fluorenes with different substituents in the 9-position, such as a 9-alkyl-9-phenyl fluorenes.

WO 2009/066061 discloses a hole transport layer comprising a polymer having a repeat unit comprising a 9,9 biphenyl fluorene repeat unit wherein the 9-phenyl rings are independently and optionally substituted.

Setayesh et al, J. Am. Chem. Soc. 2001, 123, 946-953 discloses polyfluorene with a polyphenylene dendron side chain.

US 2007/145886 discloses an organic electroluminescent device comprising a material to reduce triplet-triplet, singlet-singlet or triplet-singlet interaction.

SUMMARY OF THE INVENTION

In a first aspect the invention provides a polymer comprising a repeat unit of formula (I):

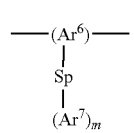

(I)

wherein $Ar^6$ and $Ar^7$ each independently represent a substituted or unsubstituted aryl or heteroaryl group; Sp represents a spacer group comprising a chain of at least 2 aliphatic carbon atoms spacing $Ar^6$ from $Ar^7$; m is at least 1; and if m is greater than 1 then $—(Ar^7)_m$ forms a linear or branched chain of $Ar^7$ groups in which $Ar^7$ in each occurrence may be the same or different.

Optionally, $Ar^6$ is a substituted or unsubstituted fluorene.
Optionally, the repeat unit of formula (I) has formula (Ia):

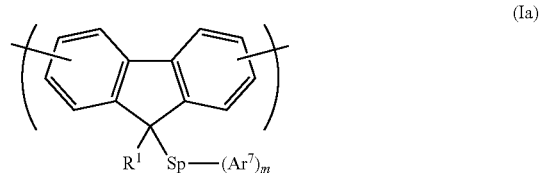

(Ia)

wherein $R^1$ is H or a substituent.
Optionally, $R^1$ is selected from the group consisting of:
a substituted or unsubstituted group $Ar^3$,
a linear or branched chain of substituted or unsubstituted $Ar^3$ groups; and
substituted or unsubstituted linear $C_{1-20}$ n-alkyl or cyclic $C_{5-12}$ alkyl wherein one or more non-adjacent C atoms of the alkyl group may be replaced with O, S, substituted N, substituted Si, C=O, —COO—, heteroaryl or aryl, and one or more of the H atoms of the alkyl group may be replaced with $C_{1-5}$ alkyl, F or an aryl or heteroaryl group,
wherein $Ar^3$ in each occurrence independently represents an aryl or heteroaryl group.
Optionally, $R^1$ has the formula $-Sp-(Ar^7)_m$.
Optionally, the repeat unit of formula (Ia) is linked to adjacent repeat units through its 2- and 7-positions.

Optionally, the repeat unit of formula (Ia) is conjugated to an aromatic or heteroaromatic group of a repeat unit adjacent to the repeat unit of formula (Ia).

Optionally, m is 1 and $Ar^7$ is a substituted or unsubstituted fluorene.

Optionally, $Ar^7$ is a group of formula (II):

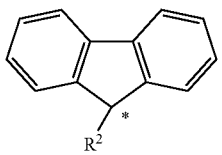

(II)

wherein $R^2$ is H or a substituent and * indicates a point of attachment to Sp.

Optionally, $R^2$ is selected from the group consisting of:
a substituted or unsubstituted group $Ar^3$,
a linear or branched chain of substituted or unsubstituted $Ar^3$ groups; and
substituted or unsubstituted linear $C_{1-20}$ n-alkyl or cyclic $C_{5-12}$ alkyl wherein one or more non-adjacent C atoms of the alkyl group may be replaced with O, S, substituted N, substituted Si, C=O, —COO—, heteroaryl or aryl, and one or more of the H atoms of the alkyl group may be replaced with $C_{1-5}$ alkyl, F or an aryl or heteroaryl group,
wherein $Ar^3$ in each occurrence independently represents an aryl or heteroaryl group.

Optionally, $Ar^7$ is a substituted or unsubstituted phenyl.

Optionally, Sp comprises a chain of at least 3 aliphatic carbon atoms.

Optionally, the aliphatic carbon atoms are $sp^3$ hybridised carbon atoms.

Optionally, Sp is a $C_{2-10}$ n-alkyl chain wherein one or more non-adjacent C atoms of the n-alkyl chain may be replaced with substituted or unsubstituted aryl or heteroaryl, O, S, substituted N, substituted Si, —C=O and —COO—, and one or more H atoms of alkyl may be replaced with $C_{1-5}$ alkyl, F or an aryl or heteroaryl group.

Optionally, Sp is a hydrocarbyl group.

Optionally, Sp is a linear or branched $C_{2-20}$ alkyl group.

Optionally, the polymer comprises a repeat unit of formula (V):

(V)

wherein $Ar^1$ and $Ar^2$ in each occurrence are independently selected from substituted or unsubstituted aryl or heteroaryl groups, n is greater than or equal to 1, preferably 1 or 2, R is H or a substituent, preferably a substituent, x and y are each independently 1, 2 or 3, and any two of groups $Ar^1$, $Ar^2$ and R may be linked by a direct bond or a divalent linking group to form a ring.

In a second aspect, the invention provides an organic electronic device comprising a polymer according to the first aspect.

Optionally according to the second aspect, the device is an organic light-emitting device comprising an anode, a cathode and a light-emitting layer between the anode and the cathode.

Optionally according to the second aspect, the light-emitting layer comprises the polymer.

Optionally according to the second aspect, the device further comprises a charge-transporting layer.

Optionally according to the second aspect, the charge-transporting layer is a hole-transporting layer between the anode and the light-emitting layer.

Optionally according to the second aspect, the hole-transporting layer comprises a polymer according to the first aspect.

In a third aspect, the invention provides a compound of Formula (Ib):

(Ib)

wherein $Ar^6$, $Ar^7$, Sp and m are as described in the first aspect, and each L is independently a polymerisable group.

Optionally according to the third aspect, each L is the same or different and is selected from leaving groups capable of participating in metal-mediated cross-coupling.

Optionally according to the third aspect, each L is the same or different and is selected from halogen, sulfonic acid esters and boronic acid and esters thereof.

In a fourth aspect, the invention provides a method of forming a polymer comprising the step of polymerizing a compound of the third aspect.

Optionally according to the fourth aspect, the compound is polymerized in the presence of a metal catalyst, optionally a palladium or nickel catalyst.

DESCRIPTION OF THE DRAWINGS

The invention will now be described in more detail with reference to the drawings, in which.

DETAILED DESCRIPTION OF THE INVENTION

Figure 1:
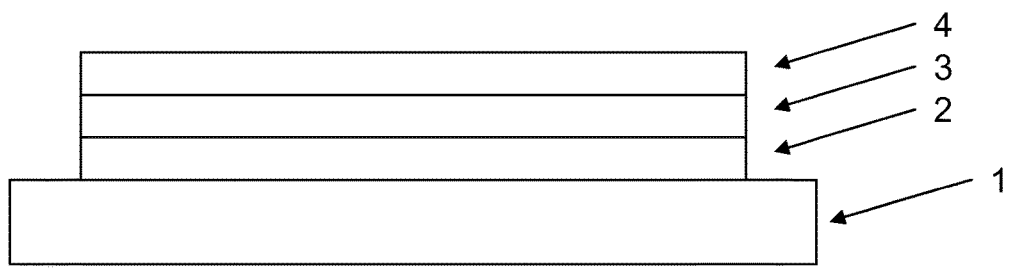
FIG. 1 is a schematic illustration of an organic light-emitting device according to an embodiment of the invention.

FIG. 1, which is not drawn to any scale, illustrates schematically an OLED according to an embodiment of the invention. The OLED is carried on substrate 1 and comprises an anode 2, a cathode 4, and a light-emitting layer 3 between the anode and the cathode.

The OLED may be provided with one or more additional layers (not shown) between the anode 2 and the cathode 4, including one or more further light-emitting layers and/or one or more charge transporting layers, charge blocking layers and/or exciton blocking layers.

The light emitting layer 3 may contain a polymer comprising a repeat unit of Formula (I). Additionally or alternatively, a charge-transporting layer or a charge blocking layer (if present) may contain a polymer comprising a repeat unit of Formula (I).

Figure 2:
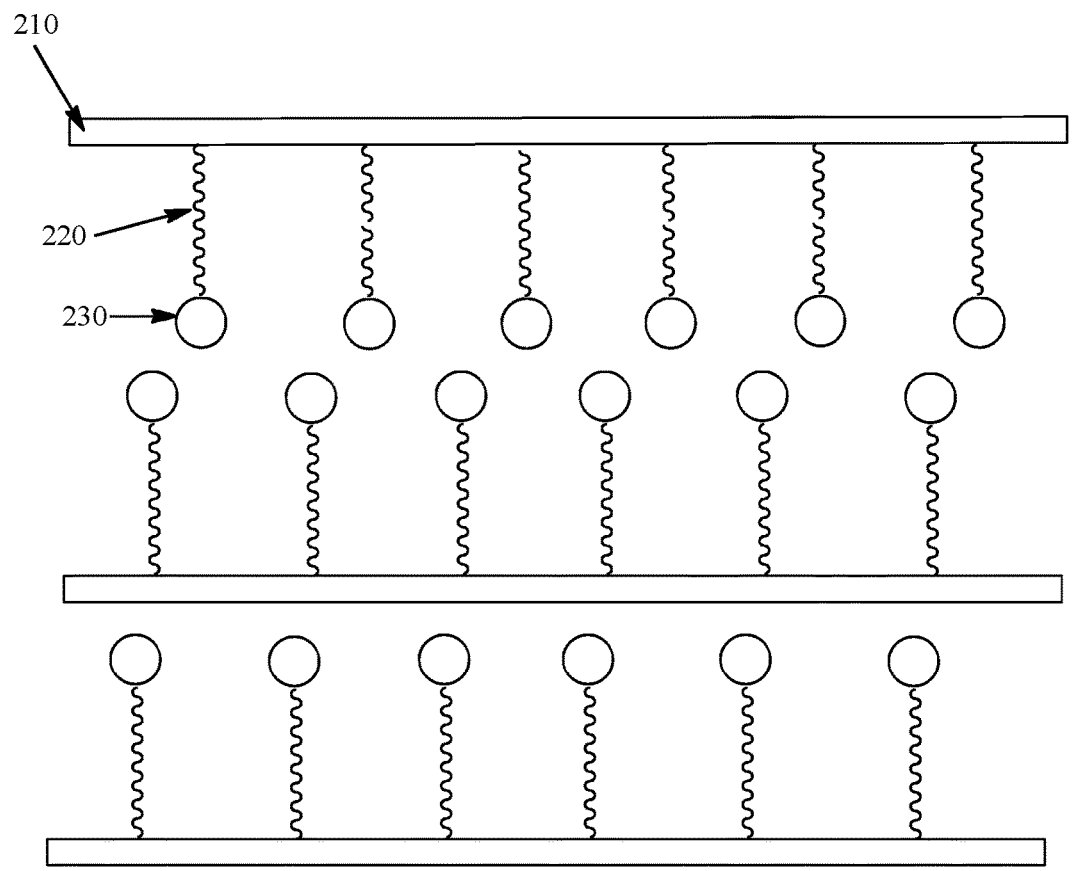
FIG. 2 is a schematic illustration of a plurality of polymer chains according to an embodiment of the invention.

With reference to FIG. 2, the polymers of the invention have a polymer backbone 210 substituted with sidechains containing aromatic or heteroaromatic group 230 spaced apart from the polymer backbone by a spacer group 220.

Without wishing to be bound by any theory, it is believed that this sidechain causes individual polymer chains to remain separate from one another, thereby preventing or reducing interaction between polymer backbones, such as exciton-exciton interactions that may involve formation of "super-excited" species that may be detrimental to the operational life of the device or to other aspects of device performance. An example of such an interaction is singlet-singlet interaction leading to singlet-singlet annihilation.

Examples of an arylene or heteroarylene unit $Ar^6$ of formula (I) in the polymer backbone are phenylene, fluorene or indenofluorene, each of which may be substituted only with a sidechain of formula -Sp-$(Ar^7)_m$, or substituted with one or more further substituents $R^1$.

Substituents $R^1$ are optionally selected from:
a substituted or unsubstituted group $Ar^3$,
a linear or branched chain of substituted or unsubstituted $Ar^3$ groups; and
substituted or unsubstituted $C_{1-20}$ n-alkyl wherein one or more non-adjacent C atoms of the n-alkyl group may be replaced with O, S, substituted N, substituted Si, C=O, —COO—, heteroaryl or aryl, and one or more of the H atoms of the n-alkyl group may be replaced with $C_{1-5}$ alkyl, F or an aryl or heteroaryl group.
wherein $Ar^3$ in each occurrence independently represents an aryl or heteroaryl group.

Substituted N or substituted Si, where present, is optionally N or Si substituted with alkyl or with phenyl. Where a C atom of the n-alkyl chain is replaced with an aryl or heteroaryl group, the aryl or heteroaryl group is preferably phenyl which may be substituted with one or more $C_{1-10}$ alkyl groups.

The spacer group Sp of formula (I) is optionally a $C_{2-10}$ n-alkyl chain wherein one or more non-adjacent C atoms of the n-alkyl chain may be replaced with substituted or unsubstituted aryl or heteroaryl, O, S, substituted N, substituted Si, —C=O and —COO—, and one or more H atoms of alkyl may be replaced with $C_{1-5}$ alkyl, F or an aryl or heteroaryl group, with the proviso that Sp contains at least two aliphatic carbon atoms spacing $Ar^6$ from $Ar^7$. Preferably, one of the at least two aliphatic carbon atoms of the spacer group Sp is bound directly to $Ar^6$.

Substituted N or substituted Si, where present, is optionally N or Si substituted with alkyl or with phenyl. Where a C atom of the n-alkyl chain is replaced with an aryl or heteroaryl group, the aryl or heteroaryl group is preferably phenyl which may be substituted with one or more $C_{1-10}$ alkyl groups.

$Ar^7$ of formula (I) is a substituted or unsubstituted aryl or heteroaryl group. In the case where $Ar^7$ is a substituted aryl or heteroaryl, $Ar^7$ may be substituted with one or more substituents selected from $R^2$. $R^2$ may be the same or different in each occurrence.

Substituents $R^2$ are optionally selected from:
a substituted or unsubstituted group $Ar^3$,
a linear or branched chain of substituted or unsubstituted $Ar^3$ groups wherein $Ar^3$ in each occurrence independently represents an aryl or heteroaryl group; and
substituted or unsubstituted $C_{1-20}$ n-alkyl wherein one or more non-adjacent C atoms of the n-alkyl group may be replaced with O, S, substituted N, substituted Si, C=O, —COO—, heteroaryl or aryl, and one or more of the H atoms of the n-alkyl group may be replaced with $C_{1-5}$ alkyl, F or an aryl or heteroaryl group, If m is greater than 1 then each $Ar^7$ may be the same or different. Optionally, each $Ar^7$ is an aromatic group. In one embodiment, each $Ar^7$ is independently selected from fluorene and phenyl.

Substituted N or substituted Si, where present, is optionally N or Si substituted with alkyl or with phenyl. Where a C atom of the n-alkyl chain is replaced with an aryl or heteroaryl group, the aryl or heteroaryl group is preferably phenyl which may be substituted with one or more $C_{1-10}$ alkyl groups.

Preferably, $Ar^7$ is not crosslinkable. Preferably, $Ar^7$ does not comprise benzocyclobutane.

Repeat units of polymers of the invention may have formula (Ia) as described above, specific examples of which include the following repeat units:

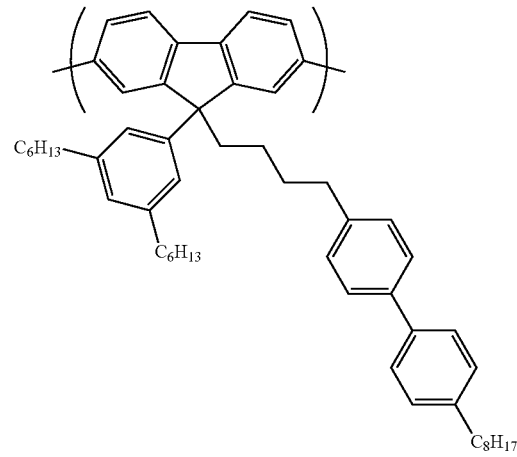

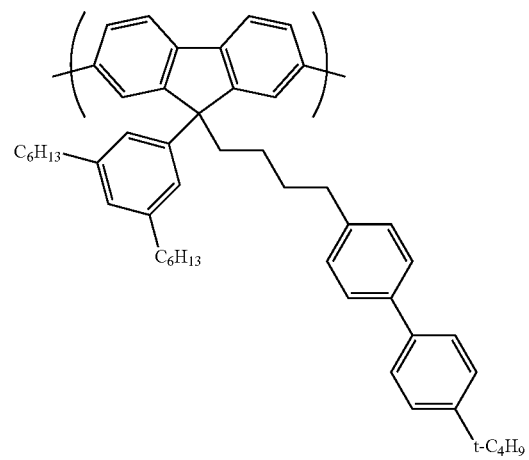

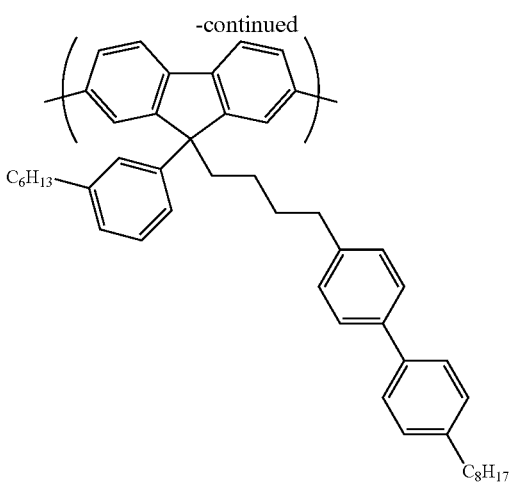

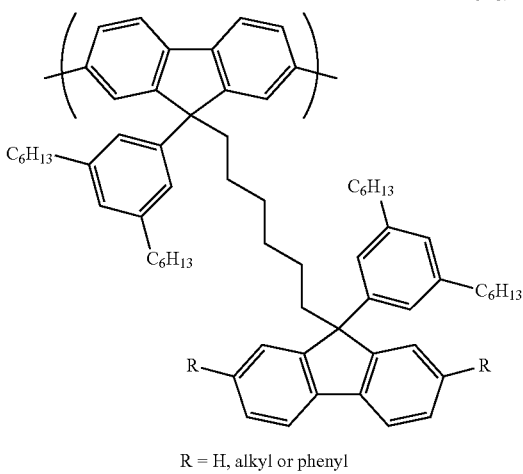

R = H, alkyl or phenyl

The repeat units exemplified above have only one group of formula -Sp-(Ar$^7$)$_m$, as described with reference to formula (I). In other embodiments, the polymer comprises fluorene repeat units wherein both substituents at the 9-position of the fluorene ring have formula -Sp-(Ar$^7$)$_m$.

In one preferred embodiment, R$^1$ is phenyl, which may be unsubstituted or substituted with one or more C$_{1-20}$ alkyl groups.

In another preferred embodiment, R$^1$ is a linear or branched chain of phenyl groups, each of which may be unsubstituted or substituted with one or more C$_{1-20}$ alkyl groups, for example:

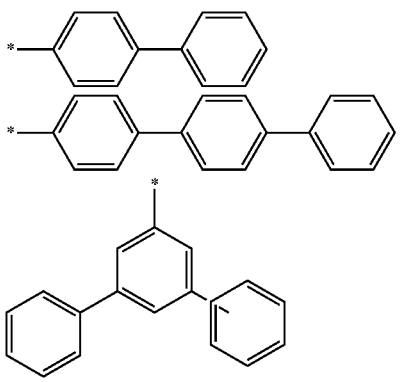

In another preferred embodiment, R$^1$ is C$_{1-20}$ alkyl, optionally C$_{2-20}$ alkyl.

These preferred substituents R$^1$ may be substituents of formula (Ia) or substituents of any other group Ar$^6$.

R$^1$ may be bound to Ar$^6$ through an sp$^2$ hybridised carbon atom of a substituted or unsubstituted aromatic or hetero aromatic group, for example phenyl, and -Sp-(Ar$^7$)$_m$ may be bound to Ar$^6$ through an sp$^3$ hybridised aliphatic carbon atom of Sp.

Preferred substituents R$^2$, where present, include substituents that are the same as preferred embodiments of R$^1$ described above.

Repeat units of formula (I) may be provided in the range of about 1 mol % to about 99 mol %. Optionally, the repeat unit of formula in an amount of at least 5 mol %, at least 10 mol % or at least 20 mol %. The copolymer may comprise one or more of hole transporting, electron transporting and/or light-emitting repeat units such as disclosed in, for example, WO 00/55927 and U.S. Pat. No. 6,353,083.

Electron transporting, hole transporting and/or light-emitting units may be provided as repeat units in the polymer backbone, such as disclosed in U.S. Pat. No. 6,353,083, or may be provided as functional units pendent from the polymer backbone.

The polymer is preferably at least partially conjugated along its backbone. Repeat units of formula (I) may be conjugated to at least one, and optionally both, of the repeat units on either side of it in the polymer backbone.

Polymers of the invention may be used as, for example: a repeat unit of a light-emitting polymer, in which this repeat unit and/or another repeat unit is emissive; a repeat unit of a hole transporting polymer comprising one or more hole-transporting repeat units; a repeat unit of an electron-transporting polymer; or as a repeat unit of a host polymer for use in combination with a light-emitting dopant. An emissive polymer may emit, without limitation, red, green or blue light.

Hole Transporting and/or Light-Emitting Repeat Units

One class of hole transporting and/or light-emitting repeat units, for example blue and/or green light-emitting repeat units, are substituted or unsubstituted (hetero)arylamines. Suitable repeat units include repeat units of formula (V):

wherein Ar$^1$ and Ar$^2$ in each occurrence are independently selected from substituted or unsubstituted aryl or heteroaryl groups, n is greater than or equal to 1, preferably 1 or 2, R in each occurrence is H or a substituent, preferably a substituent, and x and y are each independently 1, 2 or 3.

Exemplary groups R include alkyl, Ar$^3$, or a branched or linear chain of Ar$^3$ groups, for example —(Ar$^3$)$_v$, wherein Ar$^3$ in each occurrence is independently selected from aryl or heteroaryl and v is at least 1, optionally 1, 2 or 3.

Any of Ar$^1$, Ar$^2$ and Ar$^3$ may independently be substituted with one or more substituents. Preferred substituents are selected from the group R$^3$ consisting of:
  alkyl wherein one or more non-adjacent C atoms may be replaced with O, S, substituted N, C=O and —COO— and one or more H atoms of the alkyl group may be replaced with F or aryl or heteroaryl that may be unsubstituted or substituted with one or more groups R$^4$, aryl or heteroaryl that may be unsubstituted or substituted with one or more groups R$^4$, NR$^5_2$, OR$^5$, SR$^5$, fluorine, nitro and cyano; wherein each R$^4$ is independently alkyl in which one or more non-adjacent C atoms may be replaced with O, S, substituted N, C=O and —COO— and one or more H atoms of the alkyl group may be replaced with F, and each R$^5$ is independently selected from the group consisting of alkyl and aryl or heteroaryl that may be unsubstituted or substituted with one or more alkyl groups.

R may comprise a crosslinkable-group, for example a group comprising a polymerisable double bond such and a vinyl or acrylate group, or a benzocyclobutane group.

Any of the aryl or heteroaryl groups in the repeat unit of Formula (V) may be linked by a direct bond or a divalent linking atom or group. Preferred divalent linking atoms and groups include O, S; substituted N; and substituted C.

Where present, substituted N or substituted C of R$^3$, R$^4$ or of the divalent linking group may independently in each occurrence be NR$^6$ or CR$^6_2$ respectively wherein R$^6$ is alkyl or substituted or unsubstituted aryl or heteroaryl. Optional substituents for aryl or heteroaryl groups R$^6$ may be selected from R$^4$ or R$^5$.

In one preferred arrangement, R is Ar$^3$ and each of Ar$^1$, Ar$^2$ and Ar$^3$ are independently and substituted or unsubstituted with one or more C$_{1-20}$ alkyl groups.

Particularly preferred units satisfying Formula 1 include units of Formulae 1-3:

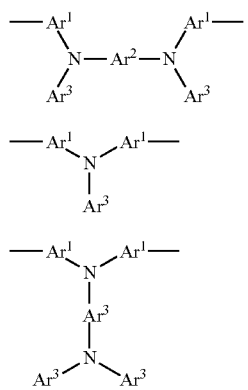

wherein Ar$^1$ and Ar$^2$ are as defined above; and Ar$^3$ is substituted or unsubstituted aryl or heteroaryl. Where present, preferred substituents for Ar$^3$ include substituents as described for Ar$^1$ and Ar$^2$, in particular alkyl and alkoxy groups.

Ar$^1$, Ar$^2$ and Ar$^3$ are preferably phenyl, each of which may independently be substituted with one or more substituents as described above.

In another preferred arrangement, aryl or heteroaryl groups of formula (V) are phenyl, each phenyl group being substituted or unsubstituted with one or more alkyl groups.

In another preferred arrangement, Ar$^1$, Ar$^2$ and Ar$^a$ are phenyl, each of which may be substituted with one or more C$_{1-20}$ alkyl groups, and v=1.

In another preferred arrangement, Ar$^1$ and Ar$^2$ are phenyl, each of which may be substituted with one or more C$_{1-20}$ alkyl groups, and R is 3,5-diphenylbenzene wherein each phenyl may be substituted with one or more alkyl groups.

In another preferred arrangement, Ar$^1$, Ar$^2$ and Ar$^3$ are phenyl, each of which may be substituted with one or more C$_{1-20}$ alkyl groups, n=1 and Ar$^1$ and Ar$^2$ are linked by O to form a phenoxazine group.

The polymer may comprise one, two or more different repeat units of formula (V). For example, the polymer may comprise one repeat unit of formula (V) to provide hole transport and another repeat unit of formula (V) to provide light-emission.

The repeat units of formula (V) may be provided in any amount, for example in the range of about 1 mol % to about 70 mol %. In the case where the polymer is used as a light-emitting material, the repeat units of formula (V) may be present in an amount less than 50 mol %, for example less than 20 mol % or less than 10 mol %.

Arylene Repeat Units

Electron transport may be provided by a conjugated chain of arylene repeat units, for example a conjugated chain comprising one or more of fluorene, indenofluorene, and phenylene repeat units (including repeat units of formula I), each of which may optionally be substituted by, for example, alkyl or alkoxy.

Exemplary fluorene repeat units, other than repeat units of formula (I), include repeat units of formula (IV):

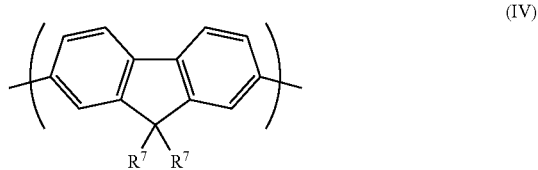

wherein the two groups R$^7$, which may be the same or different, are each H or a substituent and wherein the two groups R$^7$ may be linked to form a ring.

Each R$^7$ is optionally selected from the group consisting of hydrogen; substituted or unsubstituted Ar$^3$ or a linear or branched chain of substituted or unsubstituted Ar$^3$ groups, wherein Ar$^3$ is as described above and is preferably substituted or unsubstituted phenyl, fluorene, anthracene, naphthalene or phenanthrene; and substituted or unsubstituted alkyl wherein one or more non-adjacent C atoms of the alkyl group may be replaced with O, S, substituted N, C=O and —COO—.

In the case where R$^7$ comprises alkyl, optional substituents of the alkyl group include F, CN, nitro, and aryl or heteroaryl that may be unsubstituted or substituted with one or more groups R$^4$ wherein R$^4$ is as described above.

In the case where R$^7$ comprises aryl or heteroaryl, each aryl or heteroaryl group may independently be substituted. Preferred optional substituents for the aryl or heteroaryl groups include one or more substituents R$^3$ as described with reference to formula (V).

Optional substituents for the fluorene unit, other than substituents R$^7$, are preferably selected from the group consisting of alkyl wherein one or more non-adjacent C atoms may be replaced with O, S, substituted N, C=O and —COO—; substituted or unsubstituted aryl, for example phenyl that may be unsubstituted or substituted with one or more alkyl groups; substituted or unsubstituted heteroaryl; fluorine, cyano and nitro.

Where present, substituted N in repeat units of formula (IV) may independently in each occurrence be NR$^5$ or NR$^6$.

In one preferred arrangement, at least one of R$^1$ and R$^2$ comprises a substituted or unsubstituted C$_1$-C$_{20}$ alkyl or a substituted or unsubstituted aryl group, in particular phenyl substituted with one or more $C_{1-20}$ alkyl groups.

Repeat units of formula (IV) are optionally present in the polymer in an amount of at least 50 mol %, optionally more than 50 mol %.

Analogous repeat units may be as described above with reference to the 2,7-linked unit of formula (IV), but wherein the repeat unit is linked through its 2- and 6-positions; its 3- and 6-positions; or its 3- and 7-positions. Such analogous repeat units may reduce the extent of conjugation of the polymer as compared to 2,7-fluorene units.

Another exemplary class of arylene repeat units is phenylene repeat units, such as phenylene repeat units of formula (VI):

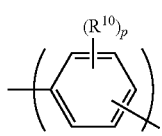

(VI)

wherein p is 0, 1, 2, 3 or 4, optionally 1 or 2, and $R^{10}$ independently in each occurrence is a substituent, optionally a substituent $R^7$ as described above, for example $C_{1-20}$ alkyl, and phenyl that is unsubstituted or substituted with one or more $C_{1-20}$ alkyl groups.

The repeat unit of formula (VI) may be 1,4-linked, 1,2-linked or 1,3-linked.

If the repeat unit of formula (VI) is 1,4-linked and if p is 0 then the extent of conjugation of repeat unit of formula (VI) to one or both adjacent repeat units may be relatively high.

If p is at least 1, and/or the repeat unit is 1,2- or 1,3-linked, then the extent of conjugation of repeat unit of formula (VI) to one or both adjacent repeat units may be relatively low. In one optional arrangement, the repeat unit of formula (VI) is 1,3-linked and p is 0, 1, 2 or 3. In another optional arrangement, the repeat unit of formula (VI) has formula (VIa):

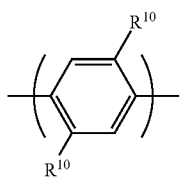

(VIa)

Another exemplary arylene repeat unit has formula (VII):

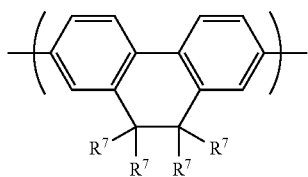

(VII)

wherein $R^5$ is as described with reference to formula (IV) above. Each of the $R^7$ groups may be linked to any other of the $R^7$ groups to form a ring.

Further arylene co-repeat units include: phenanthrene repeat units; naphthalene repeat units; anthracene repeat units; and perylene repeat units. Each of these arylene repeat units may be linked to adjacent repeat units through any two of the aromatic carbon atoms of these units. Specific exemplary linkages include 9,10-anthracene; 2,6-anthracene; 1,4-naphthalene; 2,6-naphthalene; 2,7-phenanthrene; and 2,5-perylene.

Polymerisation Methods

Preferred methods for preparation of conjugated polymers comprise a "metal insertion" wherein the metal atom of a metal complex catalyst is inserted between an aryl or heteroaryl group and a leaving group of a monomer. Exemplary metal insertion methods are Suzuki polymerisation as described in, for example, WO 00/53656 and Yamamoto polymerisation as described in, for example, T. Yamamoto, "Electrically Conducting And Thermally Stable π-Conjugated Poly(arylene)s Prepared by Organometallic Processes", Progress in Polymer Science 1993, 17, 1153-1205. In the case of Yamamoto polymerisation, a nickel complex catalyst is used; in the case of Suzuki polymerisation, a palladium complex catalyst is used.

For example, in the synthesis of a linear polymer by Yamamoto polymerisation, a monomer having two reactive halogen groups is used. Similarly, according to the method of Suzuki polymerisation, at least one reactive group is a boron derivative group such as a boronic acid or boronic ester and the other reactive group is a halogen. Preferred halogens are chlorine, bromine and iodine, most preferably bromine.

It will therefore be appreciated that repeat units illustrated throughout this application may be derived from a monomer carrying suitable leaving groups. Likewise, an end group or side group may be bound to the polymer by reaction of a suitable leaving group.

Suzuki polymerisation may be used to prepare regioregular, block and random copolymers. In particular, homopolymers or random copolymers may be prepared when one reactive group is a halogen and the other reactive group is a boron derivative group. Alternatively, block or regioregular, in particular AB, copolymers may be prepared when both reactive groups of a first monomer are boron and both reactive groups of a second monomer are halogen.

As alternatives to halides, other leaving groups capable of participating in metal insertion include groups include tosylate, mesylate and triflate.

Light-Emitting Dopants

Polymers of the invention may be used as light-emitting polymer in which the fluorene unit or a co-repeat unit may be luminescent. Alternatively, the polymer may be used as a host material, for one or more fluorescent or phosphorescent light-emitting dopants.

Suitable dopants include luminescent metal complexes, for example metal complexes comprising substituted or unsubstituted complexes of formula (VI):

$$ML^1{}_qL^2{}_rL^3{}_s \qquad (VI)$$

wherein M is a metal; each of $L^1$, $L^2$ and $L^3$ is a coordinating group; q is an integer; r and s are each independently 0 or an integer; and the sum of $(a \cdot q)+(b \cdot r)+(c \cdot s)$ is equal to the number of coordination sites available on M, wherein a is the number of coordination sites on $L^1$, b is the number of coordination sites on $L^2$ and c is the number of coordination sites on $L^3$.

Heavy elements M induce strong spin-orbit coupling to allow rapid intersystem crossing and emission from triplet or higher states (phosphorescence). Suitable heavy metals M include:

lanthanide metals such as cerium, samarium, europium, terbium, dysprosium, thulium, erbium and neodymium; and d-block metals, in particular those in rows 2 and 3 i.e. elements 39 to 48 and 72 to 80, in particular ruthenium, rhodium, palladium, rhenium, osmium, iridium, platinum and gold. Iridium is particularly preferred.

Suitable coordinating groups for the f-block metals include oxygen or nitrogen donor systems such as carboxylic acids, 1,3-diketonates, hydroxy carboxylic acids, Schiff bases including acyl phenols and iminoacyl groups. As is known, luminescent lanthanide metal complexes require sensitizing group(s) which have the triplet excited energy level higher than the first excited state of the metal ion. Emission is from an f-f transition of the metal and so the emission colour is determined by the choice of the metal. The sharp emission is generally narrow, resulting in a pure colour emission useful for display applications.

The d-block metals are particularly suitable for emission from triplet excited states. These metals form organometallic complexes with carbon or nitrogen donors such as porphyrin or bidentate ligands of formula (V):

(V)

wherein $Ar^4$ and $Ar^5$ may be the same or different and are independently selected from substituted or unsubstituted aryl or heteroaryl; $X^1$ and $Y^1$ may be the same or different and are independently selected from carbon or nitrogen; and $Ar^4$ and $Ar^5$ may be fused together. Ligands wherein $X^1$ is carbon and $Y^1$ is nitrogen are particularly preferred.

Examples of bidentate ligands are illustrated below:

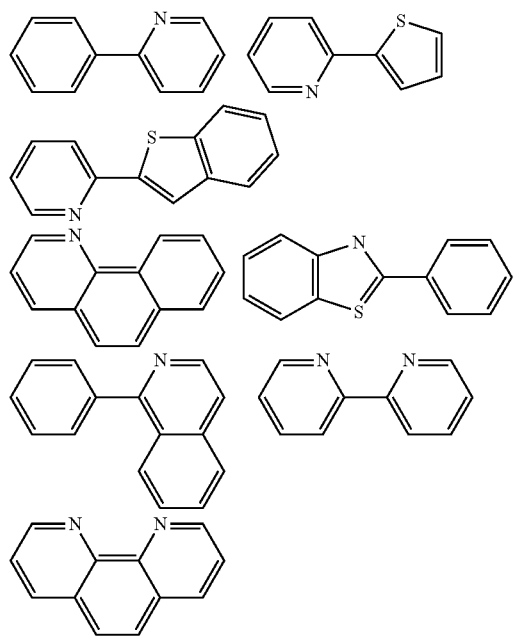

Each of $Ar^4$ and $Ar^5$ may carry one or more substituents. Two or more of these substituents may be linked to form a ring, for example an aromatic ring. Particularly preferred substituents include fluorine or trifluoromethyl which may be used to blue-shift the emission of the complex as disclosed in WO 02/45466, WO 02/44189, US 2002-117662 and US 2002-182441; alkyl or alkoxy groups as disclosed in JP 2002-324679; carbazole which may be used to assist hole transport to the complex when used as an emissive material as disclosed in WO 02/81448; bromine, chlorine or iodine which can serve to functionalise the ligand for attachment of further groups as disclosed in WO 02/68435 and EP 1245659; and dendrons which may be used to obtain or enhance solution processability of the metal complex as disclosed in WO 02/66552.

A light-emitting dendrimer typically comprises a light-emitting core bound to one or more dendrons, wherein each dendron comprises a branching point and two or more dendritic branches. Preferably, the dendron is at least partially conjugated, and at least one of the core and dendritic branches comprises an aryl or heteroaryl group.

Other ligands suitable for use with d-block elements include diketonates, in particular acetylacetonate (acac); triarylphosphines and pyridine, each of which may be substituted.

Main group metal complexes show ligand based, or charge transfer emission. For these complexes, the emission colour is determined by the choice of ligand as well as the metal.

A wide range of fluorescent low molecular weight metal complexes are known and have been demonstrated in organic light emitting devices [see, e. g., Macromol. Sym. 125 (1997) 1-48, U.S. Pat. No. 5,150,006, U.S. Pat. No. 6,083,634 and U.S. Pat. No. 5,432,014]. Suitable ligands for di or trivalent metals include: oxinoids, e. g. with oxygen-nitrogen or oxygen-oxygen donating atoms, generally a ring nitrogen atom with a substituent oxygen atom, or a substituent nitrogen atom or oxygen atom with a substituent oxygen atom such as 8-hydroxyquinolate and hydroxyquinoxalinol-10-hydroxybenzo (h) quinolinato (II), benzazoles (III), schiff bases, azoindoles, chromone derivatives, 3-hydroxy-flavone, and carboxylic acids such as salicylato amino carboxylates and ester carboxylates. Optional substituents include halogen, alkyl, alkoxy, haloalkyl, cyano, amino, amido, sulfonyl, carbonyl, aryl or heteroaryl on the (hetero) aromatic rings which may modify the emission colour.

The host and the light-emitting dopant may be physically mixed. Alternatively, the light-emitting dopant may be chemically bound to the host. In the case of a polymeric host, the light-emitting dopant may be chemically bound as a substituent attached to the polymer backbone, incorporated as a repeat unit in the polymer backbone or provided as an end-group of the polymer as disclosed in, for example, EP 1245659, WO 02/31896, WO 03/18653 and WO 03/22908.

This binding may result in more efficient transfer of excitons from the host polymer to the light emitting dopant because it may provide intramolecular exciton transfer pathways unavailable to a corresponding mixed system.

Moreover, binding may be beneficial for processing reasons. For example, if the light emitting dopant has low solubility then binding it to a soluble polymer allows the light emitting dopant to be carried in solution by the charge transporting material, enabling device fabrication using solution processing techniques. Furthermore, binding the light emitting dopant to the polymer may prevent phase separation effects in solution-processed devices that may be detrimental to device performance.

More than one light-emitting dopant may be used. For example, red, green and blue light-emitting dopants may be used to obtain white light emission. The 9-alkyl-9-aryl fluorene unit may also emit light, in particular blue light, that may be combined with emission from one or more further dopants to achieve white light emission.

Hole Injection Layers

A conductive hole injection layer, which may be formed from a conductive organic or inorganic material, may be provided between the anode 2 and the light-emitting layer 3 illustrated in FIG. 1 to assist hole injection from the anode into the layer or layers of semiconducting polymer. Examples of doped organic hole injection materials include substituted or unsubstituted, doped poly(ethylene dioxythiophene) (PEDT), in particular PEDT doped with a charge-balancing polyacid such as polystyrene sulfonate (PSS) as disclosed in EP 0901176 and EP 0947123, polyacrylic acid or a fluorinated sulfonic acid, for example Nafion®; polyaniline as disclosed in U.S. Pat. No. 5,723,873 and U.S. Pat. No. 5,798,170; and substituted or unsubstituted polythiophene or poly(thienothiophene). Examples of conductive inorganic materials include transition metal oxides such as VOx MoOx and RuOx as disclosed in Journal of Physics D: Applied Physics (1996), 29(11), 2750-2753.

Charge Transporting Layers

A hole transporting layer may be provided between the anode 2 and the light-emitting layer 3. Likewise, an electron transporting layer may be provided between the cathode and the light-emitting layer.

Similarly, an electron blocking layer may be provided between the anode 2 and the light-emitting layer 3 and a hole blocking layer may be provided between the cathode 4 and the light-emitting layer 3. Transporting and blocking layers may be used in combination. Depending on its HOMO and LUMO levels, a single layer may both transport one of holes and electrons and block the other of holes and electrons.

If present, a hole transporting layer located between anode 2 and light-emitting layer 3 preferably has a HOMO level of less than or equal to 5.5 eV, more preferably around 4.8-5.5 eV. HOMO levels may be measured by cyclic voltammetry, for example.

If present, an electron transporting layer located between light-emitting layer 3 and cathode 4 preferably has a LUMO level of around 3-3.5 eV. For example, a layer of a silicon monoxide or silicon dioxide or other thin dielectric layer having thickness in the range of 0.2-2 nm is provided between light-emitting layer 3 and layer 4.

A hole transporting layer and/or an electron transporting layer may contain a polymer comprising repeat units of formula (I).

Cathode

Cathode 4 is selected from materials that have a workfunction allowing injection of electrons into the light-emitting layer. Other factors influence the selection of the cathode such as the possibility of adverse interactions between the cathode and the light-emitting material. The cathode may consist of a single material such as a layer of aluminium. Alternatively, it may comprise a plurality of metals, for example a bilayer of a low workfunction material and a high workfunction material such as calcium and aluminium as disclosed in WO 98/10621; elemental barium as disclosed in WO 98/57381, Appl. Phys. Lett. 2002, 81(4), 634 and WO 02/84759; or a thin layer of metal compound, in particular an oxide or fluoride of an alkali or alkali earth metal, to assist electron injection, for example lithium fluoride as disclosed in WO 00/48258; barium fluoride as disclosed in Appl. Phys. Lett. 2001, 79(5), 2001; and barium oxide. In order to provide efficient injection of electrons into the device, the cathode preferably has a workfunction of less than 3.5 eV, more preferably less than 3.2 eV, most preferably less than 3 eV. Work functions of metals can be found in, for example, Michaelson, J. Appl. Phys. 48(11), 4729, 1977.

The cathode may be opaque or transparent. Transparent cathodes are particularly advantageous for active matrix devices because emission through a transparent anode in such devices is at least partially blocked by drive circuitry located underneath the emissive pixels. A transparent cathode comprises a layer of an electron injecting material that is sufficiently thin to be transparent. Typically, the lateral conductivity of this layer will be low as a result of its thinness. In this case, the layer of electron injecting material is used in combination with a thicker layer of transparent conducting material such as indium tin oxide.

It will be appreciated that a transparent cathode device need not have a transparent anode (unless, of course, a fully transparent device is desired), and so the transparent anode used for bottom-emitting devices may be replaced or supplemented with a layer of reflective material such as a layer of aluminium. Examples of transparent cathode devices are disclosed in, for example, GB 2348316.

Encapsulation

Organic optoelectronic devices tend to be sensitive to moisture and oxygen. Accordingly, the substrate preferably has good barrier properties for prevention of ingress of moisture and oxygen into the device. The substrate is commonly glass, however alternative substrates may be used, in particular where flexibility of the device is desirable. For example, the substrate may comprise a plastic as in U.S. Pat. No. 6,268,695 which discloses a substrate of alternating plastic and barrier layers or a laminate of thin glass and plastic as disclosed in EP 0949850.

The device may be encapsulated with an encapsulant (not shown) to prevent ingress of moisture and oxygen. Suitable encapsulants include a sheet of glass, films having suitable barrier properties such as silicon dioxide, silicon monoxide, silicon nitride or alternating stacks of polymer and dielectric as disclosed in, for example, WO 01/81649 or an airtight container as disclosed in, for example, WO 01/19142. In the case of a transparent cathode device, a transparent encapsulating layer such as silicon monoxide or silicon dioxide may be deposited to micron levels of thickness, although in one preferred embodiment the thickness of such a layer is in the range of 20-300 nm. A getter material for absorption of any atmospheric moisture and/or oxygen that may permeate through the substrate or encapsulant may be disposed between the substrate and the encapsulant.

Solution Processing

Suitable solvents for forming compositions of the polymer for solution processing include many common organic solvents, such as mono- or poly-alkylbenzenes such as toluene and xylene.

Particularly preferred solution deposition techniques including printing and coating techniques such spin-coating and inkjet printing.

Spin-coating is particularly suitable for devices wherein patterning of the electroluminescent material is unnecessary—for example for lighting applications or simple monochrome segmented displays.

Inkjet printing is particularly suitable for high information content displays, in particular full colour displays. A device may be inkjet printed by providing a patterned layer over the first electrode and defining wells for printing of one colour (in the case of a monochrome device) or multiple colours (in the case of a multicolour, in particular full colour device). The patterned layer is typically a layer of photoresist that is patterned to define wells as described in, for example, EP 0880303.

As an alternative to wells, the ink may be printed into channels defined within a patterned layer. In particular, the photoresist may be patterned to form channels which, unlike wells, extend over a plurality of pixels and which may be closed or open at the channel ends.

Other solution deposition techniques include dip-coating, roll printing and screen printing.

EXAMPLES

Monomer Example 1

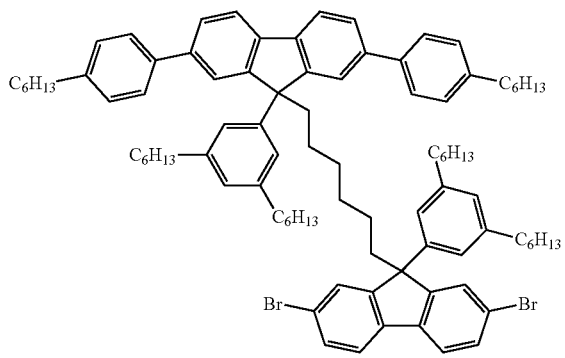

Monomer Example 1, illustrated above, was prepared as follows.

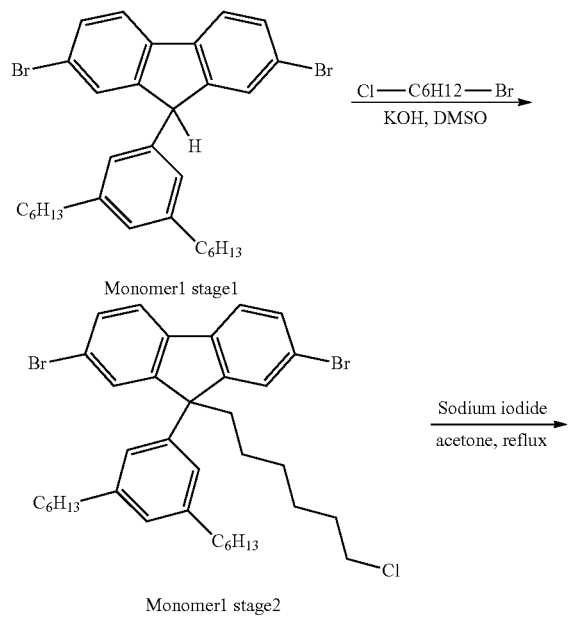

Monomer1 stage1

Monomer1 stage2

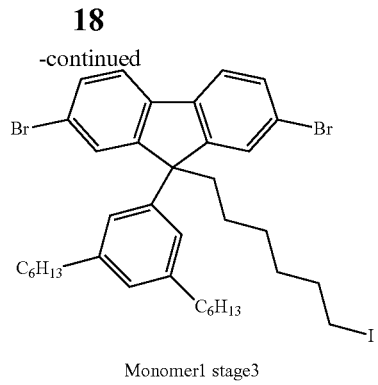

Monomer1 stage3

Monomer 1 Stage 1

1-bromo-3,5-di(n-hexyl)benzene was dissolved in anhydrous THF (2 L) under nitrogen. The mixture was cooled to <−75° C. n-Butyllithium was added drop-wise to the stirred reaction mixture at such a rate as to keep the temperature below −70° C. 2,7-dibromofluorenone (142 g, 0.42 mol) was added in portions to the reaction mixture ensuring the internal temperature did not rise above −70° C. The mixture was allowed to warm to room temperature overnight with stirring, was then cooled to <0° C. and then quenched by the addition of dilute hydrochloric acid (2M, 100 ml). The mixture was allowed to warm to room temperature. The crude mixture was transferred to a round-bottomed flask and the solvent removed under vacuum. Hexane (2.5 L) was added and the unreacted dibromofluorenone solid was removed by filtration using a fluted filter paper. The hexane filtrate was then washed with water (2×150 ml) and brine (200 ml). The hexane solution was passed through a silica plug, which was eluted with hexane then hexane: DCM (1:1, 3.5 L) and the filtrates were combined and evaporated to yield 2,7-dibromo-9-hydroxy-9-(3,5-di-n-hexylphenyl)fluorene.

To a mixture of the 2,7-dibromo-9-hydroxy-9-(3,5-di-n-hexylphenyl)fluorene and trifluoroacetic acid was added triethylsilane. The mixture was then stirred at room temperature for 62 h under nitrogen. The reaction mixture was quenched into water (1 L) and extracted with hexane. The combined hexane phases were washed with a potassium phosphate solution (500 ml, 10% wt/vol). The aqueous phase was removed and the hexane phase was washed with brine (300 ml). The organic phase was evaporated under vacuum to give an oil. The oil was dissolved in dichloromethane (~400 ml) and precipitated into methanol (2.5 L). The solid was filtered off, rinsed with methanol, and dried under vacuum at 60° C. to yield the Monomer1 stage 1 material. This was used directly in the next stage.

Monomer1 Stage2:

Monomer1 stage1 (119.0 g, 0.2094 mol) was transferred dissolved in anhydrous THF (1.0 L) under nitrogen. The reaction vessel was cooled to approx. 10° C. (ice/salt bath). Potassium-tert-butoxide (46.98 g, 0.4187 mol, 2.0 eq) was added to the cooled mixture in portions. The reaction mixture was allowed to warm to room temperature and stirred for 2 hrs. 1-Bromo-6-chlorohexane (37.50 ml, 0.2512 mol, 1.2 eq) was added to the blood-red coloured mixture and stirred at room temperature overnight. After completion (in process check by tlc; GC-MS confirmed reaction was 95% complete) the reaction mixture was filtered and evaporated on the rotavaporator to give a red oil (260 g). The red oil was dissolved in hexane (300 ml) and passed through a silica plug (Ø 10 cm, 8 cm height, eluent DCM:hexane, 1:4). The filtrate was evaporated to give an orange oil (130 g). A second silica plug was applied under the same conditions, to give a yellow oil (106 g). The oil was further purified by column chromatography (toluene:hexane, 5:95). To remove a dimeric impurity, the product was distilled repeatedly. The colourless oil crystallizes to give a crystalline solid (65.75 g, 46% yield, 99.15% HPLC), which is Monomer1 stage2. This was used for the next step in this purity.

Monomer1 Stage3:

To a solution of monomer1 stage2 (65.75 g, 0.0957 mol) in acetone (400 ml) was added sodium iodide (43.03 g, 0.2871 mol, 3 eq.) in acetone (200 ml). The reaction mixture was heated to 80° C. (oilbath). The reaction was monitored by GC-MS. After 3 days, a precipitate had formed (sodium chloride). The reaction was stopped, cooled to room temperature and the product was extracted into hexane (2×250 ml), washed with water (4×200 ml) to remove the sodium chloride and then passed through a silica plug (Ø 10 cm, 6 cm high) eluting with hexane, then hexane:dichloromethane 1:1, 300 ml). The filtrate was evaporated to give a colourless oil, which solidified on standing to give a white solid (76 g). Trituration in methanol (300 ml) gave Monomer1 stage3 as a colourless powder (69 g, 93% yield, 99.06% HPLC). The product was used directly in the next stage.

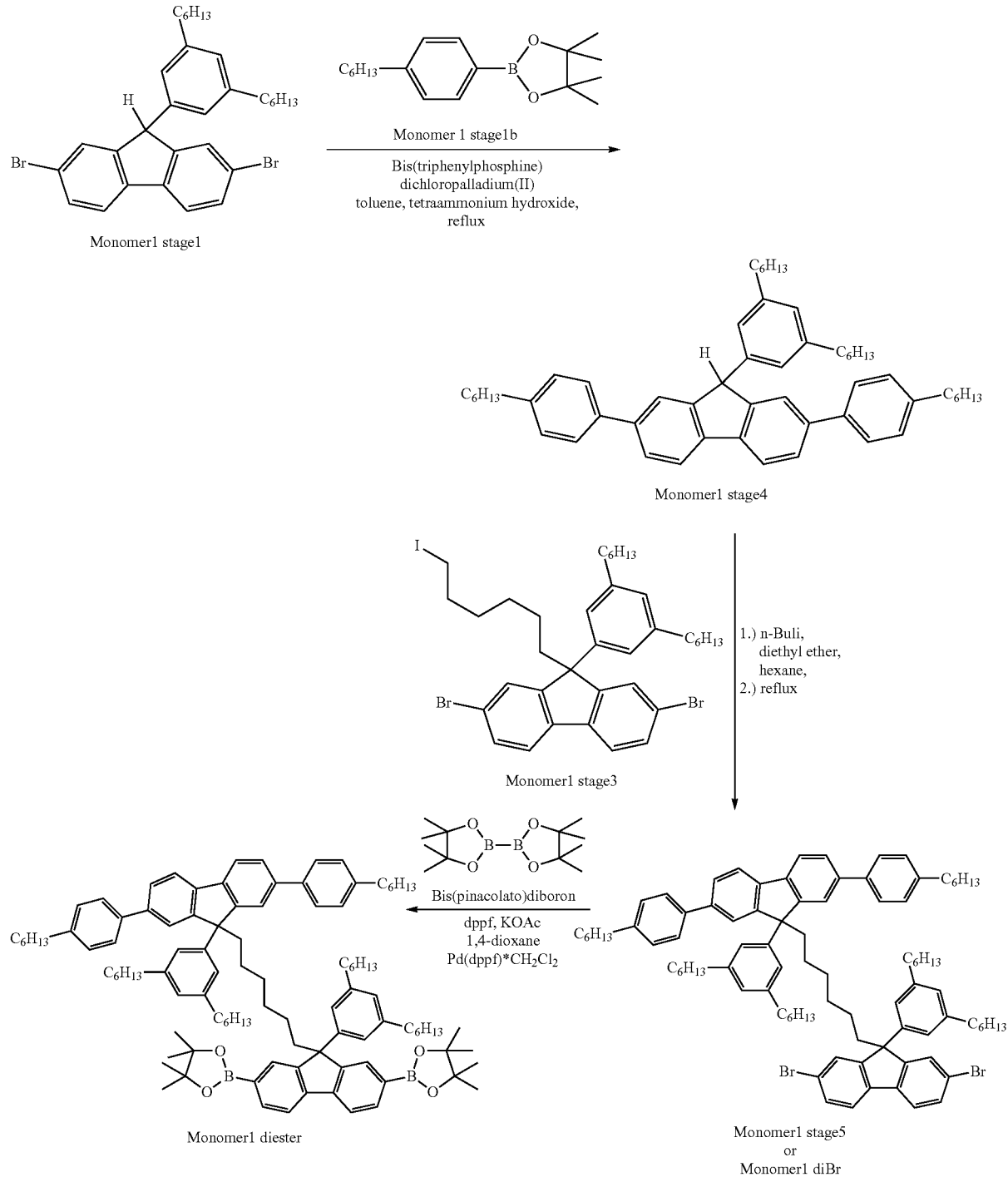

Monomer1 Stage4

Monomer1 stage1 (70.60 g, 0.1242 mol) and 4-hexylphenylboronic acid pinacol ester (78.76 g, 0.2732 mol, 2.2 eq.) were dissolved in toluene (2.0 L) and nitrogen was bubbled through the reaction mixture for 1 hr. To the reaction mixture were added bis(triphenylphosphine)dichloropalladium(II) (1.3076 g, 0.00186 mol, 0.015 eq) and tetraethylammonium hydroxide (351 ml, 0.4968 mol, 4.0 eq.). The reaction mixture was then heated to reflux (oil bath @ 115° C.). After 3 days the reaction was cooled and water was added (400 ml). The mixture was separated and the organic layer was washed with water (3×400 ml), brine (400 ml) and the solvent was removed to give a black solid (115 g).

The crude product was re-dissolved in toluene (300 ml) and passed through a Florisil/Silica plug (Ø 12.5 cm, 6 & 6 cm high, DCM:hexane, 1:4) under gravity and the filtrate was evaporated to dryness to give a white solid (78 g, 97.06% HPLC), which was recrystallised from toluene:acetonitrile (1.2 L, 1:4) to give a white solid (67 g, 98.30% HPLC). Second recrystallisation from toluene:acetonitrile (1.2 L, 1:4) gave Monomer1 stage4 as a white solid (62 g, 68% yield, 98.68% HPLC).

Monomer1 Stage5 [Monomer1 Dibromide]

Monomer1 stage4 (43.95 g, 0.0601 mol, 1.1 eq.) was dissolved in anhydrous diethyl ether (300 ml) and nitrogen was bubbled through the mixture for 30 mins. The mixture was cooled to 0° C. and n-Butyllithium (24 ml, 0.0601 mol, 1.1 eq. [2.5M in hexane]) was added drop-wise to the reaction mixture. The now deep red mixture was stirred at room temperature for 1 hr. To the mixture was added dropwise a solution of Monomer1 stage3 (42.0 g, 0.05395 mol) in anhydrous hexane (300 ml), and the resulting reaction mixture was heated to 68° C. (oil bath) for 3 days. The reaction was quenched with water at 0° C., and phases were separated. The water phase was extracted with hexane (2×300 ml). The organic layers were combined, washed with water (4×100 ml) and the solvent removed to give a red oil (84 g). The crude red oil was dissolved in hexane (300 ml) and passed through a silica plug (Ø 10 cm, 7 cm high, DCM:hexane, 1:9). The solvent was removed to yield an orange oil (80 g). The oil was dissolved in hexane (600 ml) and sulphuric acid (96%, 70 ml) was added. The mixture was stirred at RT for 20 mins, transferred to a 1 L separatory funnel and the resulting biphasic mixture was separated. The organic layer was washed subsequently with water (1×200 ml), saturated sodium carbonate solution (1×200 ml) and with water (3×200 ml) until pH 6. The organic layers were evaporated to yield an orange oil (62 g, 94% HPLC). The orange oil was then dissolved in anhydrous THF (600 ml), potassium tert-butoxide (3 g) was added, and the solution stirred red coloured solution at RT for 2 hrs. Filtered crude mixture through Aluminium oxide plug (Ø 10 cm, 4 cm high, hexane, 1 L) and removed solvent on rotavaporator to give a yellow oil (56 g, 94.65% HPLC). The oil was dissolved in DCM (300 ml) and methanol (700 ml) was added. DCM was evaporated until an oil separated from the mixture and the solvent was decanted off. Repeating this procedure three times, a colourless oil (49 g, 98.55% HPLC) of Monomer1 dibromide was obtained, which was used in the subsequent step.

Monomer1 Diester

Monomer1 dibromide (22 g, 0.0159 mol) was dissolved in 1,4-dioxane (400 ml). Bis(pinacolato)diboron (8.90 g, 0.035 mol) 1,1'-bis(diphenylphosphino)ferrocene dichloropalladium(II) dichloromethane complex (Pd(dppf)$_2$*CH$_2$Cl$_2$) (0.195 g, 0.00024 mol), 1,1'-bis(diphenyl-phosphino) ferrocene (0.1324 g, 0.00024 mol) were added, and nitrogen was bubbled through the mixture for 20 minutes. Potassium acetate (9.38 g, 0.0955 mol) was added and the reaction was heated to 105° C. (oil bath) overnight. The dark brown reaction mixture was passed through a Florisil/Silica plug (Ø 10 cm, 4 & 4 cm high, Toluene, 1 L) under gravity and the filtrate was evaporated. The residue was dissolved in toluene and filtered through a plug of Florisil/Silica. Evaporation of the filtrates gave a colourless oil. The oil was triturated in methanol (300 ml) and Monomer1 diester precipitated out as an off-white solid. The product was recrystallised repeatedly from ethyl acetate:acetonitrile or toluene:acetonitrile to give Monomer1 diester (10.45 g, 45%, 99.40% HPLC).

Polymer Example 1

A polymer was prepared by Suzuki polymerisation as described in WO 00/53656 of Monomer Example 1 diester (50 mol %) with the following co-monomers:

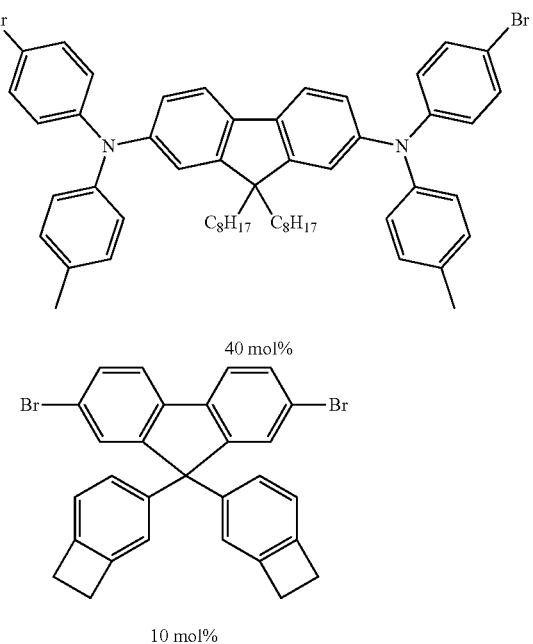

40 mol%

10 mol%

Comparative Polymer 1

A polymer was prepared as described with reference to Polymer Example 1 except that Monomer Example 1 was replaced with Comparative Monomer 1:

Comparative Monomer 1

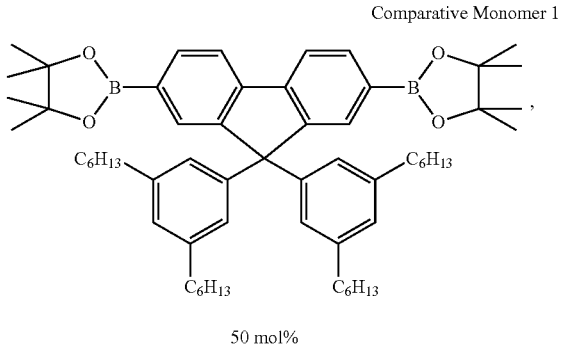

50 mol%

Device Example 1

An organic light-emitting device having the following structure was prepared:

ITO/HIL/HTL/LE/Cathode

Wherein ITO is an indium-tin oxide anode; HIL is a hole-injecting layer comprising a hole-injecting material, HTL is a hole-transporting layer formed by spin-coating Polymer Example 1 (93.5 mol %) and $C_{60}$ (6.5 mol %), LE is a light-emitting layer formed by spin-coating a light-emitting polymer and an additive polymer; and the cathode comprises a layer of metal fluoride in contact with the light-emitting layer and a layer of aluminium formed over the layer of metal fluoride.

A substrate carrying ITO was cleaned using UV/Ozone. The hole injection layer was formed to a thickness of 35 nm by spin-coating an aqueous formulation of a hole-injection material available from Plextronics, Inc. A 22 nm thick hole transporting layer was formed by spin-coating Hole Transporting Polymer 1, described below, followed by crosslinking of Hole Transporting Polymer 1 by heating. The light-emitting layer was formed by depositing a 90:10 mol % mixture of Polymer Example 1 and Additive Polymer 1 to a thickness of 65 nm by spin-coating from o-xylene solution. A cathode was formed by evaporation of a first layer of a metal fluoride to a thickness of about 2 nm, a second layer of aluminium to a thickness of about 200 nm and an optional third layer of silver.

The light-emitting polymer was formed by Suzuki polymerisation as described in WO 00/53656 of the following monomers:

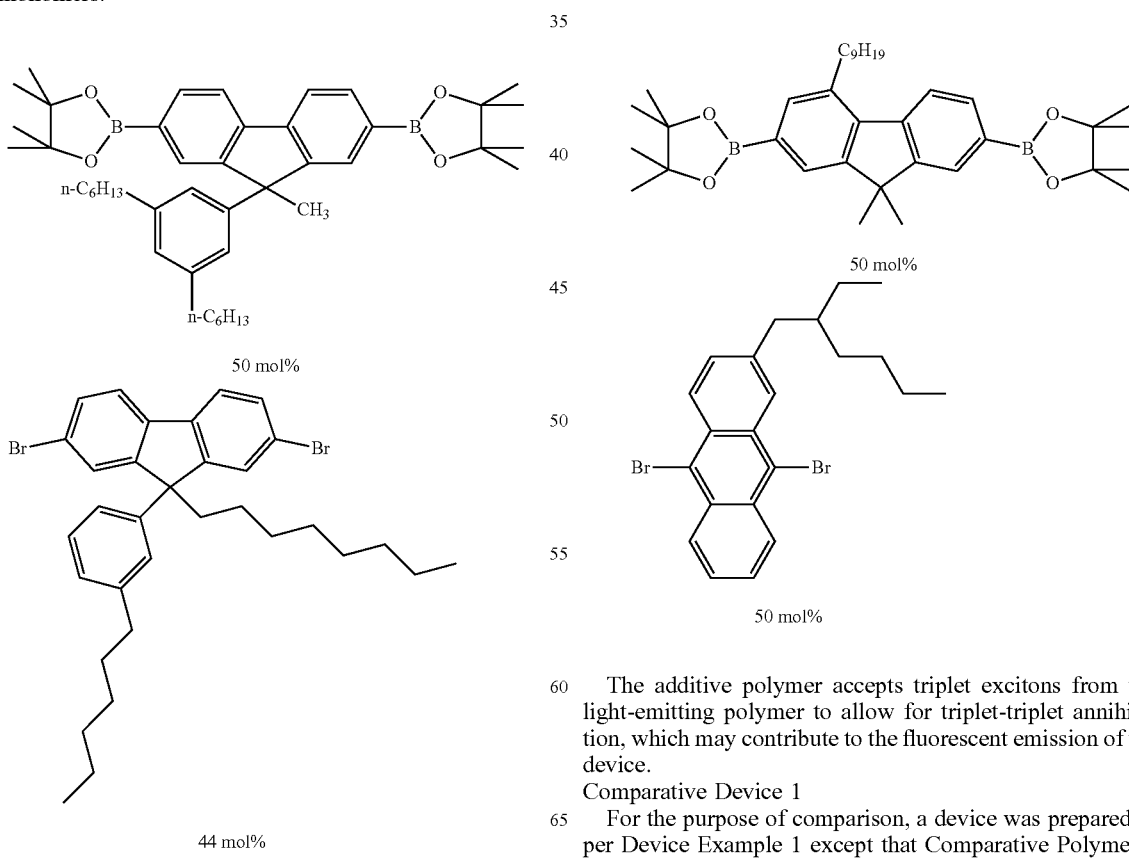

44 mol%

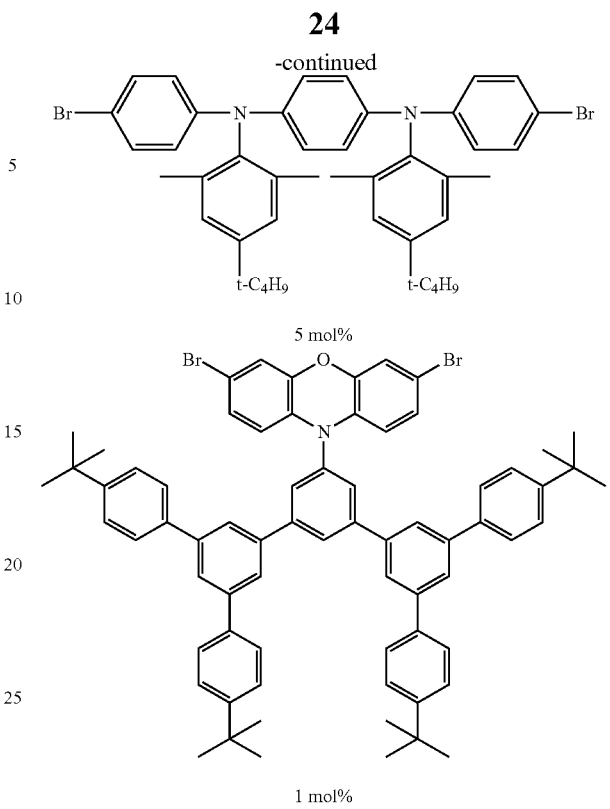

Additive Polymer 1 was formed by Suzuki polymerisation as described in WO 00/53656 of the following monomers:

The additive polymer accepts triplet excitons from the light-emitting polymer to allow for triplet-triplet annihilation, which may contribute to the fluorescent emission of the device.

Comparative Device 1

For the purpose of comparison, a device was prepared as per Device Example 1 except that Comparative Polymer 1 was used in place of Polymer Example 1.

The change in luminance over time at constant current from a starting luminance of 5000 cd/m² was measured for Device Example 1 and Comparative Device 1.

Figure 3:
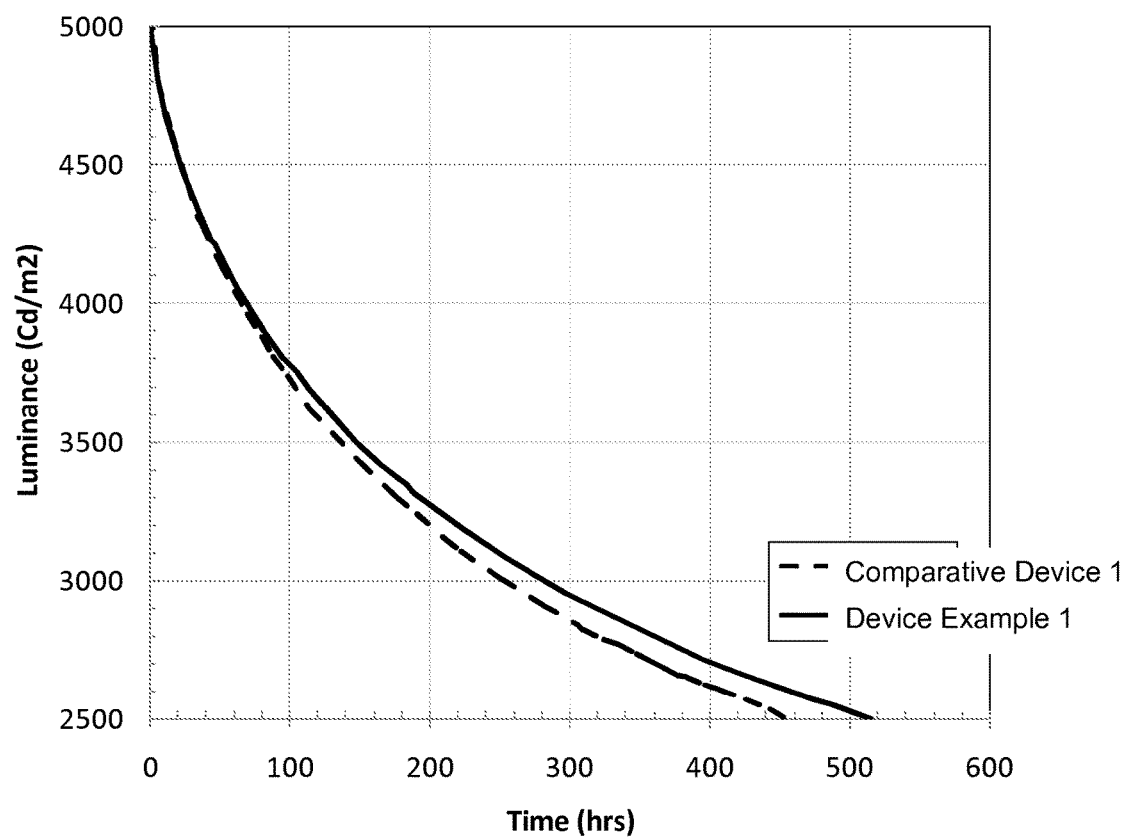
FIG. 3 is a graph of luminance vs. time of a device according to an embodiment of the invention and a comparative device.

With reference to FIG. 3, the decay in luminance is faster Comparative Device 1 than for Device Example 1.

Comparative Polymer 2

A polymer was prepared by Suzuki polymerisation as described in WO 00/53656 of the following monomers:

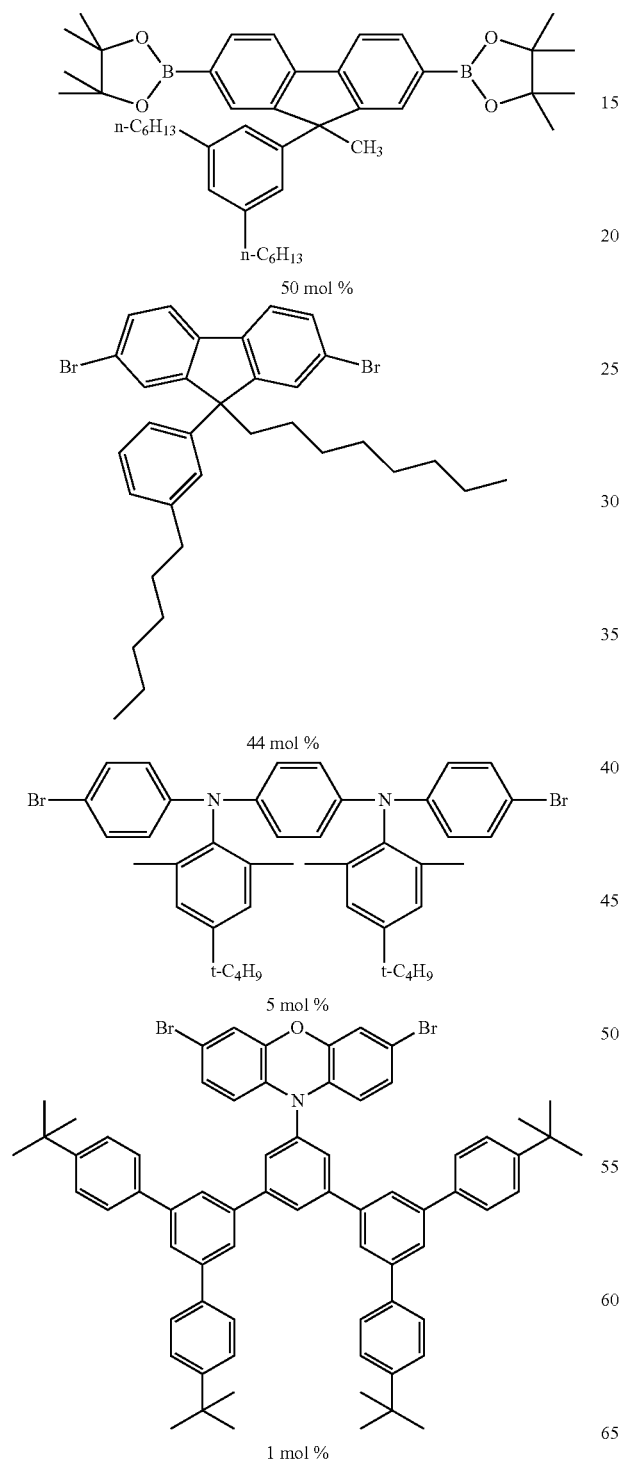

Comparative Polymer 3

A polymer was prepared by Suzuki polymerisation as described in WO 00/53656 of the following monomers:

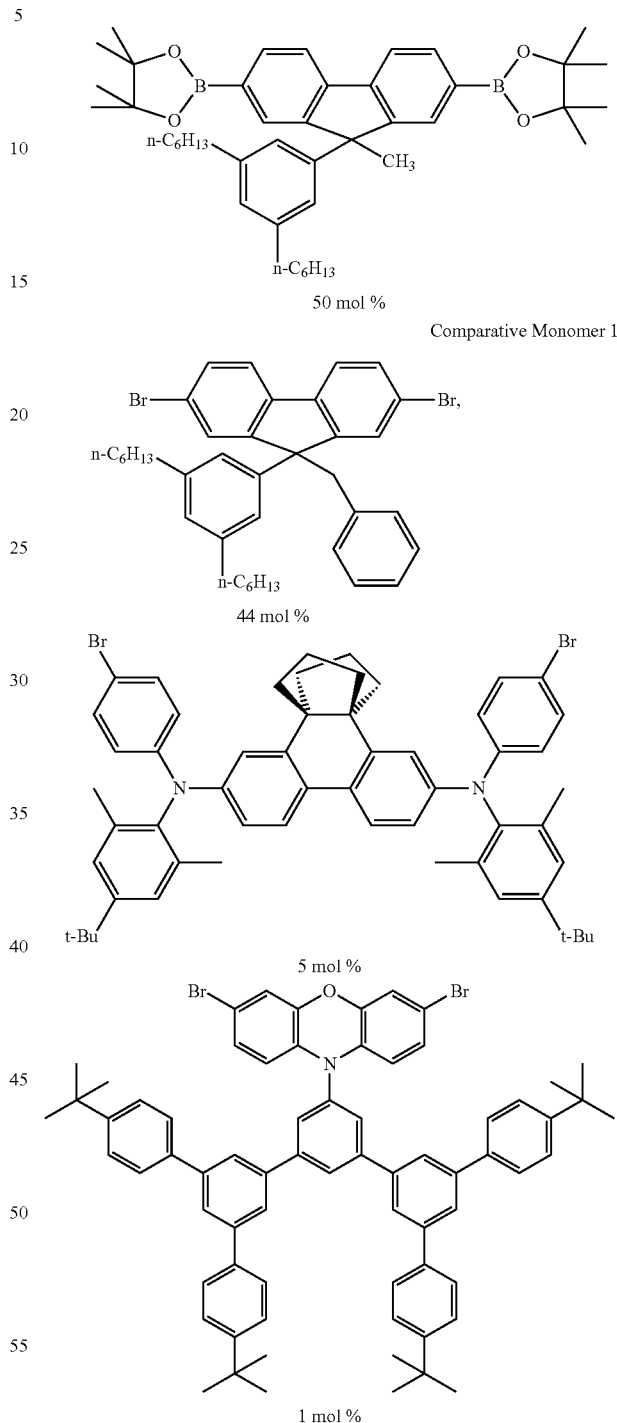

Comparative Monomer 1

Comparative Devices 2 and 3

An organic light-emitting device having the following structure was prepared:
ITO/HIL/HTL/LE/Cathode A substrate carrying ITO was cleaned using UV/Ozone. The hole injection layer was formed to a thickness of 35 nm by spin-coating an aqueous formulation of a hole-injection material available from Plextronics, Inc. A 22 nm thick hole transporting layer was formed by spin-coating Hole Transporting Polymer 1, described below, followed by crosslinking of Hole Transporting Polymer 1 by heating. The light-emitting layer was formed by depositing a 90:10 mol % mixture of Comparative Polymer 2 (for Comparative Device 2) or Comparative Polymer 3 (for Comparative Device 3) Comparative Polymer 2 and Additive Polymer 1 to a thickness of 65 nm by spin-coating from o-xylene solution. A cathode was formed by evaporation of a first layer of a metal fluoride to a thickness of about 2 nm, a second layer of aluminium to a thickness of about 200 nm and an optional third layer of silver.

Hole Transporting Polymer 1 was formed by Suzuki polymerisation as described in WO 00/53656 of the following monomers:

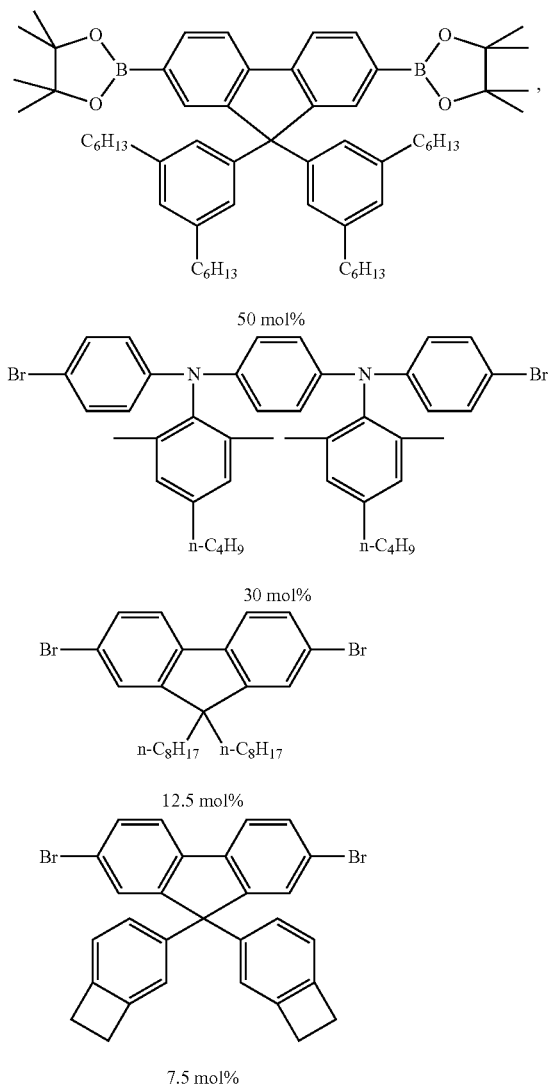

The change in luminance over time at constant current from a starting luminance of 5000 cd/m² was measured for Comparative Devices 2 and 3.

Figure 4:
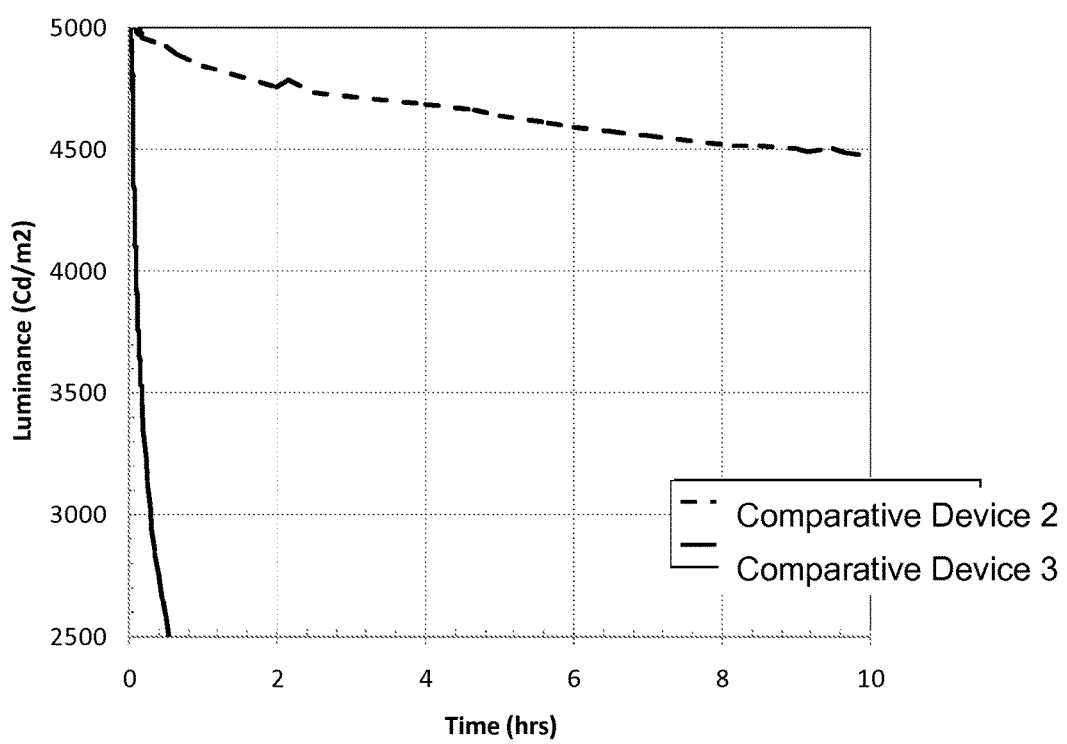
FIG. 4 is a graph of luminance vs. time of two comparative devices.

With reference to FIG. 4, the decay in luminance is much more rapid for Comparative Device 3 than for Comparative Device 2, surprisingly indicating that a spacer chain having only one carbon atom between the backbone unit and the pendant aromatic unit has a deleterious effect on device lifetime. The high rate of luminescent decay of Comparative Device 3 containing a repeat unit derived from Comparative Monomer 1 having a spacer of only one carbon atom indicates that a similar deleterious effect can be expected if such a repeat unit is used in a polymer of a hole transporting layer, in contrast to Device Example 1 wherein a hole transporting polymer having a longer spacer chain yields an increase in device lifetime.

Comparative Device 4

A device was prepared as described in Device Example 1 except that the hole transporting layer was formed by spin-coating a mixture of Hole Transporting Polymer 2 and Hole Transporting Polymer 3 in a 90:10 mol % ratio.

Hole Transporting Polymer 2 was formed by Suzuki polymerisation as described in WO 00/53656 of the following monomers:

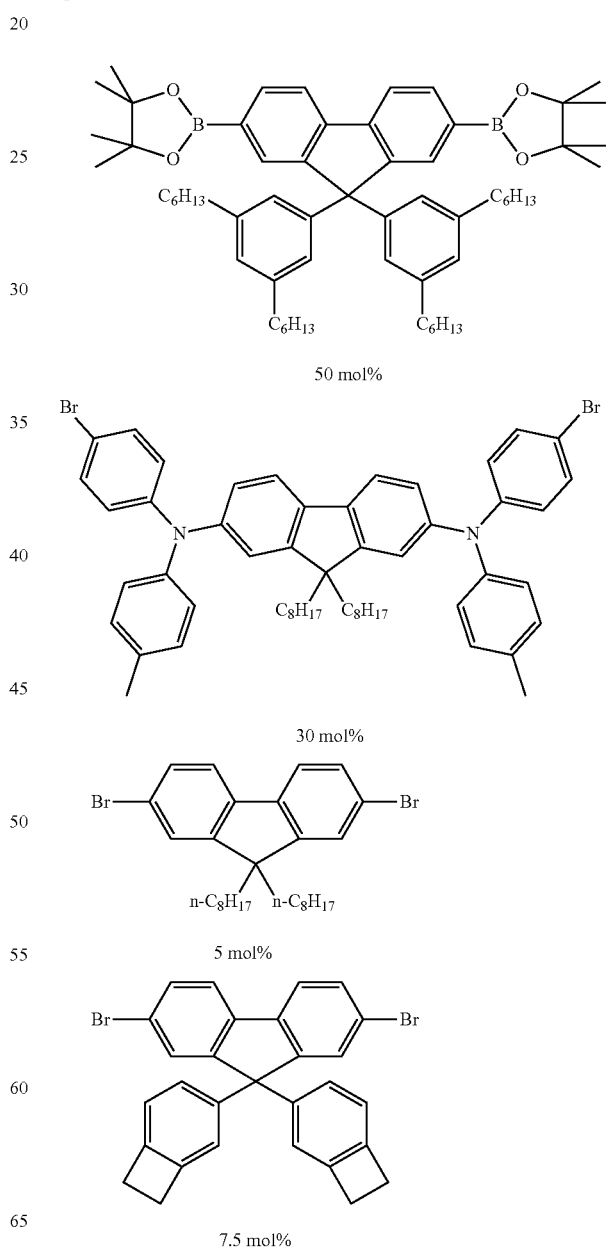

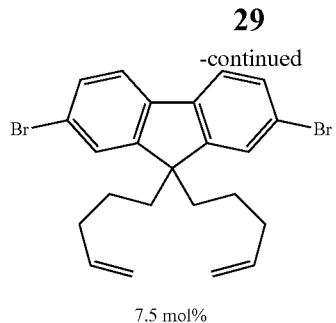

7.5 mol%

Hole Transporting Polymer 3 was formed by Suzuki polymerisation as described in WO 00/53656 of the following monomers, and 6.5 mol % dibromofullerene:

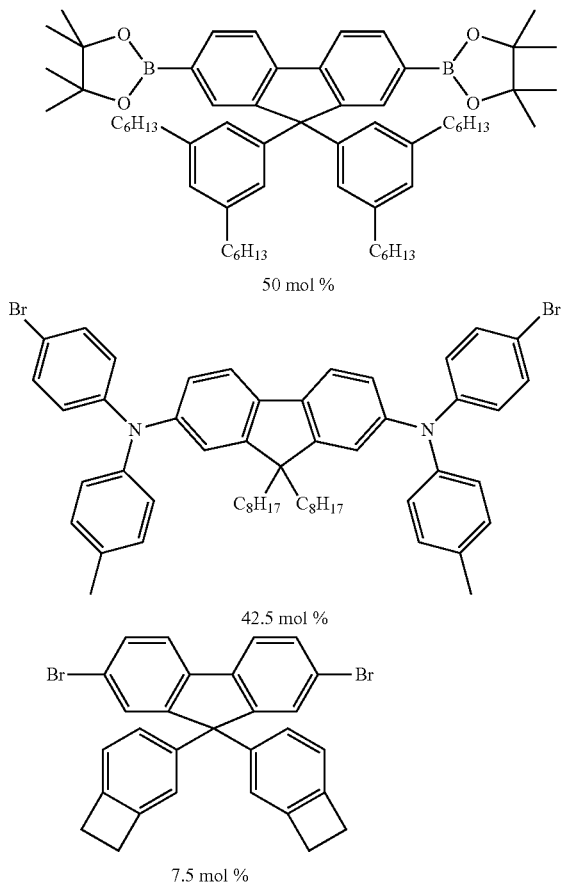

7.5 mol %

Comparative Device 5

A device was prepared as described for Comparative Device 4 except that the additive polymer was Additive Polymer 2, formed by Suzuki polymerisation of the following monomers Comparative Monomer 1

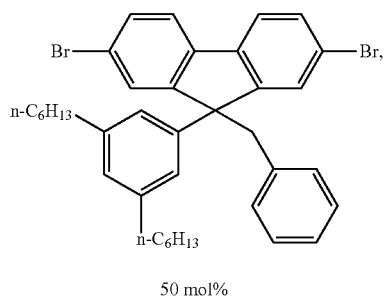

50 mol%

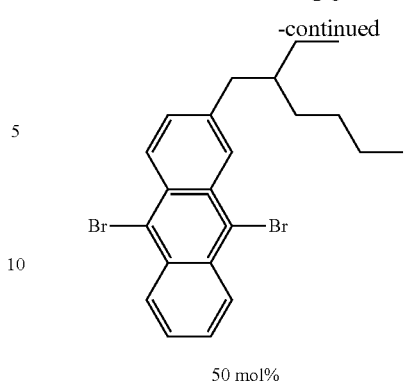

50 mol%

Figure 5:
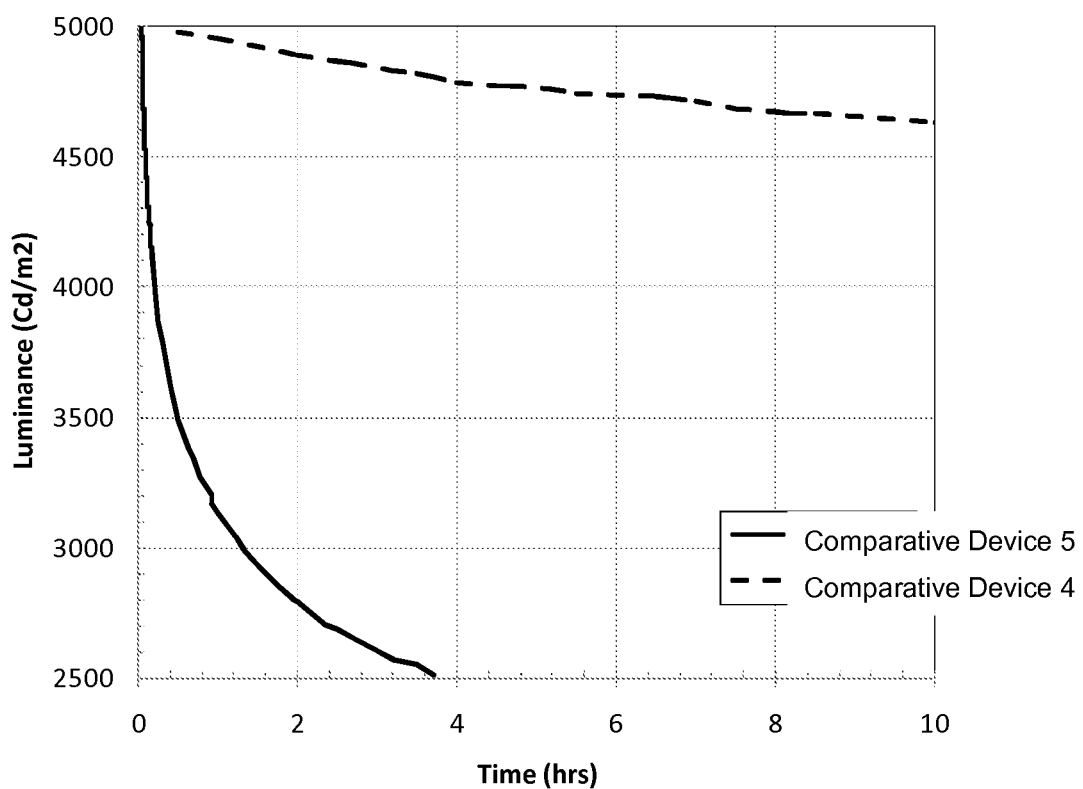
FIG. 5 is a graph of luminance vs. time of two further comparative devices.

With reference to FIG. 5, the device containing a repeat unit derived from Comparative Monomer 1 suffers from very short half life, again indicating that use of a polymer comprising a spacer chain having only one carbon atom between the backbone unit and the pendant aromatic unit has a deleterious effect on device lifetime.

Although the present invention has been described in terms of specific exemplary embodiments, it will be appreciated that various modifications, alterations and/or combinations of features disclosed herein will be apparent to those skilled in the art without departing from the scope of the invention as set forth in the following claims.

The invention claimed is:

1. A polymer comprising a repeat unit of formula (I):

(I)

wherein $Ar^6$ represents a substituted or unsubstituted aryl or heteroaryl group; $Ar^7$ is a group of formula (II):

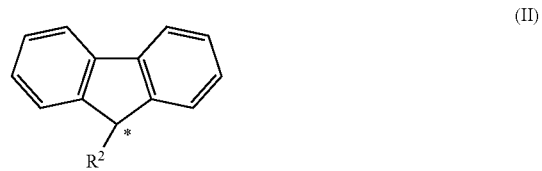

(II)

wherein $R^2$ is H or a substituent and * indicates a point of attachment to Sp; Sp represents a spacer group comprising a chain of at least 2 aliphatic carbon atoms spacing $Ar^6$ from $Ar^7$; m is 1, and wherein the polymer further comprises a repeat unit of formula (V)

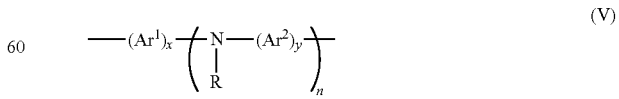

(V)

wherein $Ar^1$ and $Ar^2$ in each occurrence are independently substituted or unsubstituted aryl or heteroaryl groups, n is greater than or equal to 1, R is H or a substitutent, x and y are each independently 1, 2 or 3, and any two of groups $Ar^1$, $Ar^2$ and R are optionally linked by a direct bond or a divalent linking group to form a ring.

2. A polymer according to claim 1 wherein $Ar^6$ is a substituted or unsubstituted fluorene.

3. A polymer according to claim 2 wherein the repeat unit of formula (I) has formula (Ia):

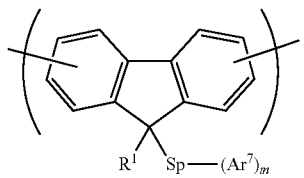

(Ia)

wherein $R^1$ is H or a substituent.

4. A polymer according to claim 3 wherein $R^1$ has the formula $-Sp-(Ar^7)_m$.

5. A polymer according to claim 1 wherein Sp comprises a chain of at least 3 aliphatic carbon atoms spacing $Ar^6$ from $Ar^7$.

6. A polymer according to claim 1 wherein Sp is a $C_{2-10}$ n-alkylene chain wherein one or more non-adjacent C atoms of the n-alkylene chain are optionally replaced with substituted or unsubstituted aryl or heteroaryl, O, S, substituted N, substituted Si, —C=O, or —COO—, and one or more H atoms of the n-alkylene chain are optionally replaced with $C_{1-5}$ alkyl, F, or an aryl or heteroaryl group.

7. An organic electronic device comprising a polymer according to claim 1.

8. An organic electronic device according to claim 7 wherein the device is an organic light-emitting device comprising an anode, a cathode and a light-emitting layer between the anode and the cathode.

9. An organic electronic device according to claim 8 wherein the light-emitting layer comprises the polymer.

10. An organic electronic device according to claim 8 wherein the device further comprises a hole-transporting layer between the anode and the light-emitting layer.

11. An organic electronic device according to claim 10 wherein the hole-transporting layer comprises a polymer comprising a repeat unit of formula (I):

(I)

wherein $Ar^6$ represents a substituted or unsubstituted aryl or heteroaryl group; $Ar^7$ is a substituted or unsubstituted fluorene; Sp represents a spacer group comprising a chain of at least 2 aliphatic carbon atoms spacing $Ar^6$ from $Ar^7$; m is at least 1; and if m is greater than 1 then $-(Ar^7)_m$ forms a linear or branched chain of $Ar^7$ groups in which $Ar^7$ in each occurrence is the same or different.

* * * * *